(12) United States Patent
Brewer et al.

(10) Patent No.: US 6,498,254 B1
(45) Date of Patent: Dec. 24, 2002

(54) ANTIRETROVIRAL COMPOUNDS AND COMPOSITIONS

(75) Inventors: Arthur D. Brewer, Puslinch (CA); Stephen E. Cantor, Cheshire, CT (US); Mark A. Dekeyser, Waterloo (CA); Arthur M. P. Doweyko, Long Valley, NJ (US); John W. Harris, Sugar Land, TX (US); John A. Lacadie, Woodbury, CT (US); James B. Pierce, Southbury, CT (US); Howard L. Plant, *deceased*, late of Milford, CT (US), by Mary Louise Jones, executor; William A. Harrison, Guelph (CA)

(73) Assignee: Uniroyal Chemical Company, Inc., Middlebury, CT (US)

( * ) Notice: Subject to any disclaimer, the term of this patent is extended or adjusted under 35 U.S.C. 154(b) by 0 days.

(21) Appl. No.: 10/021,202

(22) Filed: Oct. 29, 2001

(51) Int. Cl.$^7$ ............... A61K 31/47; C07D 215/16; C07D 211/72; C07D 211/84
(52) U.S. Cl. ............... 546/157; 546/290; 546/294; 514/312; 514/345; 514/347
(58) Field of Search ............... 546/157, 294, 546/290; 514/312, 347, 345

(56) References Cited

U.S. PATENT DOCUMENTS

| | | | | |
|---|---|---|---|---|
| 5,268,389 A | * | 12/1993 | Harrison et al. | 514/485 |
| 5,696,151 A | * | 12/1997 | Brouwer et al. | 514/448 |
| 5,945,425 A | * | 8/1999 | Moormann et al. | 514/269 |

* cited by examiner

*Primary Examiner*—Margaret Seaman
(74) *Attorney, Agent, or Firm*—Daniel Reitenbach

(57) ABSTRACT

Certain pyridine and quinoline derivatives' which inhibit replication of the retroviruses HIV-1, HIV-2 and human cytomegalovirus (HCMV) are provided. Pharmaceutical compositions useful in methods of treating or inhibiting certain retrovirus infections are described.

2 Claims, No Drawings

ANTIRETROVIRAL COMPOUNDS AND COMPOSITIONS

FIELD OF THE INVENTION

This invention relates to compounds useful as antiretroviral agents. More particularly, this invention relates to pyridine and quinoline derivatives which inhibit replication of the retroviruses HIV-1, HIV-2 and human cytomegalovirus (HCMV).

BACKGROUND OF THE INVENTION

There are currently about seven nucleoside reverse transcriptase (RT) inhibitors (NRTIs), about three nonnucleoside RT inhibitors (NNRTI) and about six protease inhibitors (PI) officially approved for the treatment of HIV-infected individuals. Reverse transcriptase and protease are virus-encoded enzymes. The clinical efficacy of the individual drugs varies depending on the nature and the molecular target of the drugs.

U.S. Pat. No. 5,268,389 describes certain thiocarboxylate ester compounds that are said to inhibit replication of HIV. It is alleged that the selectivity of these compounds for HIV-1 is due to a highly specific interaction with HIV-1 RT.

U.S. Pat. No. 5,696,151 is directed to certain carbothioamides that inhibit replication of HIV-1 and reverse transcriptase mutants thereof.

The rapid emergence of HIV-1 strains resistant to several HIV-1 -specific RT inhibitors in cell culture and in AIDS patients has caused concern for further development of these inhibitors in the clinic. See, e.g., Balzarini et al, J. Virology 67(9): 5353–5359 (1993) ("Balzarini I") and Balzarini et al, Virology 192: 246–253 (1993) ("Balzarini II").

Failure of long-term efficacy of known drugs can be associated with the appearance of dose-limiting and/or long-term side-effects, or more importantly, with the emergence of drug-resistant virus strains. Both RT inhibitors and protease inhibitors tend to select for virus strains that show a reduced susceptibility for the particular drugs. Moreover, a considerable cross-resistance exists between drugs that act against the same target.

Attempts have been made to combine various HIV-1 RT inhibitors to eliminate virus resistance. See, e.g., Balzarini I, supra. However, there is still a need for new compounds for the treatment of HIV that act at a target (either viral or cellular) that is different from those at which the existing drugs act.

It is the purpose of this invention to provide compounds which, by themselves, can inhibit or suppress the emergence of HIV-1, HIV-2 and HCMV.

SUMMARY OF THE INVENTION

This invention relates to the novel compounds 2-[[1-(5-amino-2-methylphenyl)ethyl]sulfonyl]pyridine-N-oxide [compound 1],1,4-xylyl-bis-2-sulfonyl pyridine-N-oxide [compound 23], 1,4[1,2,4,5-tetramethylbenzyl]-bis-(2'-sulfonylpyridine-N-oxide) [compound 25], 2-(4'-tert-pentylphenylmethylsulfonyl)pyridine-N-oxide [compound 40], 2[1-(9-anthryl)methylsulfonyl]pyridine-N-oxide [compound 51], ethyl-N-[4-(pyridyl-N-oxide-2-sulfonylmethyl)phenylcarbonyl]carbamate [compound 60], 2-[(3-methoxy-4-benzyloxy)phenylmethylsulfonyl] pyridine-N-oxide [compound 61], 2-[[(2-nitro-5-methylphenyl)methyl]sulfonyl]pyridine-N-oxide [compound 62], 2-[[[2,5-bis(1-methylethyl)-4-bromophenyl]methyl]sulfonyl]pyridine-N-oxide [compound 63], 2-[[(3-nitro4-chlorophenyl)methyl] sulfonyl]pyridine-N-oxide [compound 64], 2-[[(3,5-dinitrophenyl)methyl]sulfonyl]pyridine-N-oxide [compound 65], 2-[[(3-methyl-4-nitrophenyl)methyl] sulfonyl]pyridine-N-oxide [compound 66], 2-[[(3-nitro-4-methylphenyl)methyl]sulfonyl]pyridine-N-oxide [compound 67], 2-[[(2-chloro-4-nitrophenyl)methyl] sulfonyl]pyridine-N-oxide [compound 69], 2-[(2,5-dimethylphenyl)chloromethylsulfonyl]-6-methylpyridine-N-oxide [compound73], 2-[1-(2,5-dimethylphenyl)ethylsulfonyl]-6-chloropyridine-N-oxide [compound 76], 2-(2,5-dimethylphenylmethylsulfonyl)-6-chloropyridine-N-oxide [compound 77], 2-[1-(2,5-dimethylphenyl) ethylsulfonyl]-4,6-dimethylpyridine-N-oxide [compound 81], 2[(2,5-dimethylphenyl)chloromethylsulfonyl]pyridine [compound 106], 8-ethyl-4-methyl-2-[(1-phenylethyl) sulfonyl]quinoline [compound 107], 2-[[1 -(2,5-dimethylphenyl)-2-methoxyethyl]sulfonyl]pyridine [compound 123], 3-chloro-2-[[1-(2,5-dimethylphenyl)ethyl] sulfonyl]pyridine-N-oxide [compound 124], 3-chloro-2-[[chloro-(2,5-dimethylpbenyl)methyl]sulfonyl]pyridine-N-oxide [compound 125], 3-chloro-2-[(phenylmethyl)thio] pyridine-N-oxide [compound 132], 3-chloro-2-[[(2,5-dimethylphenyl)methyl]thio]pyridine-N-oxide [compound 133], 4-(1,1 -dimethylethyl)-2-[(4-methoxyphenyl) methylthio]pyridine-N-oxide [compound 134], 3-chloro-2-[(phenylmethyl)sulfinyl]pyridine-N-oxide [compound 136], 2-[[(2,6-dichlorophenyl)methyl]thio]-3-methyl-pyridine-N-oxide [compound 137], 2-[[(2,6-dichlorophenyl)methyl] sulfinyl]-3-methyl-pyridine-N-oxide [compound 138], 2-[[(2,6-dichlorophenyl)methyl]sulfonyl]-3-methyl-pyridine-N-oxide [compound 139], 2[[(2,5-dimethylphenyl) methyl]thio]-1-methylpyridinium chloride [compound 142], 2-benzylthio-3-nitropyridine [compound 146], 2-((2,5-dimethylphenyl)methylthio) pyridine [compound 148], 6-chloro-(2-benzylthio)pyridine-N-oxide [compound 149], 2-(2,5-dimethylbenzylsulfonyl)pyridine [compound 150], 5-chloro-2(benzylthio) pyridine-N-oxide [compound 151], 2-(N-methyl-3-piperidylmethylthio)pyridine-N-oxide [compound 156], 2-(2,5-dimethylphenylmethylthio) pyridine hydrochloride [compound 157], 2-(1-cyano-2-phenylethenethio) pyridine-N-oxide [compound 158], 2-[1-cyano-2-(p-methoxyphenyl)ethenethio]pyridine-N-oxide [compound 159], 2-[1-cyano-2-(3,4,5-trimethoxyphenyl) ethenethio]pyridine-N-oxide [compound 160], 2-[1-(2,5-dimethylphenyl)ethylsulfonyl]pyridine [compound 161], 2-[[1-(2,5-dimethylphenyl)ethyl]thio]-4-methylquinoline [compound 162] and 2-(2,5-dimethylphenyl)methylsulfinyl) pyridine [compound 163], and pharmaceutically acceptable salts thereof The compounds of this invention are useful for inhibiting replication of HIV-1, HIV-2 and HCMV in vitro and in vivo. The compounds are also useful in the therapeutic or prophylactic treatment of diseases caused by these viruses.

This invention additionally relates to pharmaceutical compositions containing one or more of the above recited compounds and a pharmaceutically acceptable carrier.

DETAILED DESCRIPTION OF THE INVENTION

This invention relates to the following novel compounds: 2-[[1-(5-amino-2-methylphenyl)ethyl]sulfonyl]pyridine-N-oxide [compound 1], 1,4-xylyl-bis-2-sulfonyl pyridine-N-oxide [compound 23], 1,4[1,2,4,5-tetramethylbenzyl]-bis-(2'-sulfonylpyridine-N-oxide) [compound 25], 2-(4'-tert-pentylphenylmethylsulfonyl)pyridine-N-oxide [compound 40], 2[1-(9-anthryl)methylsulfonyl]pyridine-N-oxide [compound 51], ethyl-N-[4-(pyridyl-N-oxide-2-sulfonylmethyl)phenylcarbonyl]carbamate [compound 60], 2-[(3-methoxy-4-benzyloxy)phenylmethylsulfonyl] pyridine-N-oxide [compound 61], 2-[[(2-nitro-5-methylphenyl)methyl]sulfonyl]pyridine-N-oxide [compound 62], 2-[[[2,5-bis(1-methylethyl)4-bromophenyl] methyl]sulfonyl]pyridine-N-oxide [compound 63], 2-[[(3-nitro-4-chlorophenyl)methyl]sulfonyl]pyridine-N-oxide [compound 64], 2-[[(3,5-dinitrophenyl)methyl]sulfonyl] pyridine-N-oxide [compound 65], 2-[[(3-methyl-4-nitrophenyl)methyl]sulfonyl]pyridine-N-oxide [compound 66], 2-[[(3-nitro-4-methylphenyl)methyl]sulfonyl]pyridine-N-oxide [compound 67], 2-[[(2-chloro-4-nitrophenyl) methyl]sulfonyl]pyridine-N-oxide [compound 69], 2-[(2,5-dimethylphenyl)chloromethylsulfonyl]-6-methylpyridine-N-oxide [compound73], 2-[1-(2,5-dimethylphenyl) ethylsulfonyl]-6-chloropyridine-N-oxide [compound 76], 2-(2,5-dimethylphenylmethylsulfonyl)-6-chloropyridine-N-oxide [compound 77], 2-[1-(2,5-dimethylphenyl) ethylsulfonyl]-4,6-dimethylpyridine-N-oxide [compound 81], 2[(2,5-dimethylphenyl)chloromethylsulfonyl]pyridine [compound 106], 8-ethyl-4-methyl-2-[(1-phenylethyl) sulfonyl]quinoline [compound 107], 2-[[1-(2,5-dimethylphenyl)-2-methoxyethyl]sulfonyl]pyridine [compound 123], 3-chloro-2-[[1-(2,5-dimethylphenyl)ethyl] sulfonyl]pyridine-N-oxide [compound 124], 3-chloro-2-[[chloro-(2,5-dimethylphenyl)methyl]sulfonyl]pyridine-N-oxide [compound 125], 3-chloro-2-[(phenylmethyl)thio] pyridine-N-oxide [compound 132], 3-chloro-2-[[(2,5-dimethylphenyl)methyl]thio]pyridine-N-oxide [compound 133], 4-(1,1-dimethylethyl)-2-[(4-methoxyphenyl) methylthio]pyridine-N-oxide [compound 134], 3-chloro-2-[(phenylmethyl)sulfinyl]pyridine-N-oxide [compound 136], 2-[[(2,6-dichlorophenyl)methyl]thio]-3-methyl-pyridine-N-oxide [compound 1371, 2-[[(2,6-dichlorophenyl)methyl] sufionyl]-3-methyl-pyridine-N-oxide [compound 138], 2-[[(2,6-dichlorophenyl)methyl]sulfonyl]-3-methyl-pyridine-N-oxide [compound 139], 2[[(2,5-dimethylphenyl) methyl]thio]-1-methylpyridinium chloride [compound 142], 2-benzylthio-3-nitropyridine [compound 146], 2-((2,5-dimethylphenyl) methylthio)pyridine [compound 148], 6-chloro-(2-benzylthio)pyridine-N-oxide [compound 149], 2-(2,5-dimethylbenzylsulfonyl) pyridine [compound 150], 5-chloro-2(benzylthio)pyridine-N-oxide [compound 151], 2-(N-methyl]-3-piperidylmethylthio)pyridine-N-oxide [compound 156], 2-(2,5-dimethylphenylmethylthio) pyridine hydrochloride [compound 157], 2-(1-cyano-2-phenylethenethio) pyridine-N-oxide [compound 158], 2-[1-cyano-2-(p-methoxyphenyl)ethenethio]pyridine-N-oxide [compound 159], 2-[1-cyano-2-(3,4,5-trimethoxyphenyl) ethenethio]pyridine-N-oxide [compound 160], 2-[1-(2,5-dimethylphenyl)ethylsulfonyl]pyridine [compound 161], 2-[[1-(2,5-dimethylphenyl)ethyl]thio]-4-methylquinoline [compound 162] and 2-(2,5-dimethylphenyl)methylsulfinyl) pyridine [compound 163] and pharmaceutically acceptable salts thereof.

It will be apparent to those of skill in the art that certain compounds herein may have at least one asymmetrical carbon atom and therefore all isomers, including diastereomers and rotational isomers of such compounds are contemplated as being part of this invention. The invention includes (+)- and (–)-isomers in both pure form and in admixture, including racemic mixtures. Isomers can be prepared using conventional techniques, either by reacting optically pure or optically enriched starting materials or by separating isomers of a compound herein. Those skilled in the art will appreciate that for some compounds herein, one isomer may show greater pharmacological activity than other isomers.

It will also be apparent to those of skill in the art that certain compounds herein can exist in unsolvated and solvated forms, including hydrated forms. In general, the solvated forms, with pharmaceutically acceptable solvents such as water, ethanol and the like, are equivalent to the unsolvated forms for purposes of this invention.

It will also be apparent to those of skill in the art that certain compounds herein with a basic group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

It will also be apparent to those of skill in the art that certain compounds herein may be acidic (e.g., compounds containing a carboxyl group). Acidic compounds according to the present invention can form pharmaceutically acceptable salts with inorganic and organic bases. Examples of such salts are the sodium, potassium, calcium, aluminum, lithium, gold and silver salts. Also included are salts formed with pharmaceutically acceptable amines such as ammonia, alkyl amines, hydroxyalkylamines, N-methylglucamine, and the like.

Compounds such as those disclosed herein may be prepared by a variety of methods known to those skilled in the art. For example, U.S. Pat. Nos. 3,960,542, 4,019,893, 4,050,921, and 4,294,970 the contents of each being incorporated herein by reference, describe methods of preparing 2-thio-, 2-sulfinyl-, and/or 2-sulfonyl-pyridine N-oxide derivatives. For example, the parent 2-thiopyridine N-oxides may be prepared, e.g., by two procedures: (1) the reaction of 2-chloropyridine N-oxide with the appropriate mercaptan in the presence of an acid acceptor such as an alkaline earth hydroxide; (2) reaction of the sodium salt of 2-mercaptopyridine N-oxide with a suitable halide preferably of, but not limited to, the benzyl type. The yields of the two procedures are comparable.

The aryl (or heteroaryl) alkylthiopyridines produced above may be oxidized by methods well known to those skilled in the art. The oxidation involves the conversion of both the sulfur and nitrogen to their higher oxidative states in a single preparative step. In this case the products are sulfones as the sequence of oxidation proceeds from sulfide→sulfoxide→sulfone→sulfone N-oxide. The oxidant most generally employed, but not limited to, is 30–50% hydrogen peroxide in glacial acetic acid. In excess of three equivalents of peroxide is necessary. The conversion of the aryl (or heteroaryl) alkylthiopyridine-N-oxides to analogous sulfinyl or sulfonyl compound may be accomplished by employing one or two equivalents of an oxidizing agent selected from, but not necessarily limited to, hydrogen peroxide, peracetic acid, and the aromatic peroxy acids. The ratio of peroxide to substrate varies with the desired product.

The solvents employed may vary with the oxidant as described in the literature (Katritsky and Lagowski, Chemistry of the Heterocyclic N-Oxides, Academic Press, 1971). Glacial acetic acid and water are preferred when hydrogen peroxide is used and a nonpolar solvent such as chloroform is preferred for use with the aromatic peroxy acids. When water is employed as a solvent, a catalyst of the nature of a tungsten, vanadium, zirconium or molybdenum salt (U.S. Pats. Nos. 3,005,852, 3,006,962, and 3,006,963 and British Pat. No. 1,335,626; the contents of each being incorporated by reference herein) is generally used. Temperature and time are a function of the sulfide employed with the range varying from about 50° C. to reflux in the case of water and acetic acid to about 0° to about 60° C. with chloroform.

The synthesis of 2-(alpha-aryl-alpha-chloromethyl sulfonyl) pyridine-N-oxides is also known and described in U.S. Pat. No. 4,360,677 the contents of which are incorporated by reference herein. The types of starting materials generally employed in the preparation of these compounds are known to those skilled in the art. These parent 2-aryl methylsulfonylpyridine-N-oxides may be prepared by methods described in U.S. Pat. No. 3,960,542. Their subsequent conversion to (alphachloromethylsulfonyl)pyridine-N-oxides may be carried out using a modification of a known procedure. (C. Y. Meyers, et al., J. Org. Chem., 91,7510 (1969); C. Y. Meyers, et al., Tetrahedron Lett., 1105 (1974); the contents of each being incorporated by reference herein). The solvent, N,N-dimethylformamide, is used without drying. Sodium hydroxide (97 –98%) is freshly ground to a powder before use, care being taken to avoid prolonged exposure to moisture. Temperature may generally be maintained from about −5° to about +5° C., with reaction times between about 25 and about 35 min.

The synthesis of substituted pyridine N-oxide compounds is described in U.S. Pat. No. 4,394,155 and foreign patent publication EP 36388 the contents of each being incorporated by reference herein. The substituted pyridine N-oxide compounds are generally prepared, e.g., by first preparing the appropriate thio compound. An essentially equimolar amount of an alkali metal alkoxide is added with stirring at room temperature under an atmosphere of nitrogen to the substituted or non-substituted benzylmercaptan dissolved in a suitable solvent (such as a $C_1$ to $C_4$ aliphatic alcohol, preferably methanol). The resulting solution is added slowly to a solution of a substituted pyridine N-oxide hydrochloride, which has been treated with an essentially equimolar amount of alkali metal alkoxide. The molar ratio of mercaptide anion to pyridine N-oxide is maintained at about 1, and stirring, nitrogen atmosphere and reaction at room temperature are also maintained throughout the complete reaction. After all the reactants have been combined, the reaction mixture is refluxed from about one to about six hours. The thio product which precipitates when the reaction mixture is poured into a large excess of ice water is filtered, washed several times with water, air dried and recrystallized from an alcohol such as wet ethanol.

The thio compound may be oxidized to the desired sulfinyl or sulfonyl compound by known means, e.g. the thio compound dissolved in excess chloroform is stirred into a chloroform solution of m-chloroperbenzoic acid at about −10° to about 10° C. The reaction vessel is stoppered and kept at about 0° C. for about 24 hr. The by-product, m-chlorobenzoic acid, is removed by filtration and the remaining chloroform solution washed thoroughly with aqueous sodium bicarbonate solution, then water. The chloroform solution is dried (e.g. with anhydrous magnesium sulfate) and the solvent evaporated. The final product may be recrystallized from a suitable solvent (e.g. lower alcohol).

The compounds of the present invention can be administered in any conventional dosage form known to those skilled in the art. Pharmaceutical compositions containing the compounds herein can be prepared using conventional pharmaceutically acceptable excipients and additives and conventional techniques. Such pharmaceutically acceptable excipients and additives include non-toxic compatible fillers, binders, disintegrants, buffers, preservatives, antioxidants, lubricants, flavorings, thickeners, coloring agents, emulsifiers and the like. All routes of administration are contemplated including, but not limited to, parenteral, transdermal, subcutaneous, intramuscular, sublingual, inhalation, rectal and topical.

Thus, appropriate unit forms of administration include oral forms such as tablets, capsules, powders, cachets, granules and solutions or suspensions, sublingual and buccal forms of administration, aerosols, implants, subcutaneous, intramuscular, intravenous, intranasal, intraoccular or rectal forms of administration.

When a solid composition is prepared in the form of tablets, e.g., a wetting agent such as sodium lauryl sulfate can be added to micronized or non-micronized compounds herein and mixed with a pharmaceutical vehicle such as silica, gelatine starch, lactose, magnesium stearate, talc, gum arabic or the like. The tablets can be coated with sucrose, various polymers, or other appropriate substances. Tablets can be treated so as to have a prolonged or delayed activity and so as to release a predetermined amount of active principle continuously or at predetermined intervals, e.g., by using ionic resins and the like.

A preparation in the form of gelatin capsules may be obtained, e.g., by mixing the active principle with a diluent, such as a glycol or a glycerol ester, and incorporating the resulting mixture into soft or hard gelatin capsules.

A preparation in the form of a syrup or elixir can contain the active principle together, e.g., with a sweetener, methylparaben and propylparaben as antiseptics, flavoring agents and an appropriate color.

Water-dispersible powders or granules can contain the active principle mixed, e.g., with dispersants, wetting agents or suspending agents, such as polyvinylpyrrolidone, as well as with sweeteners and/or other flavoring agents.

Rectal administration may be provided by using suppositories which may be prepared, e.g., with binders melting at the rectal temperature, for example cocoa butter or polyethylene glycols.

Parenteral, intranasal or intraocular administration may be provided by using, e.g., aqueous suspensions, isotonic saline solutions or sterile and injectable solutions containing pharmacologically compatible dispersants and/or solubilizers, for example, propylene glycol or polyethylene glycol.

Thus, to prepare an aqueous solution for intravenous injection, it is possible to use a co-solvent, e.g., an alcohol such as ethanol or a glycol such as polyethylene glycol or propylene glycol, and a hydrophilic surfactant such as Tween® 80. An oily solution injectable intramuscularly can be prepared, e.g., by solubilizing the active principle with a triglyceride or a glycerol ester.

Topical administration can be provided by using, e.g., creams, ointments or gels.

Transdermal administration can be provided by using patches in the form of a multilaminate, or with a reservoir, containing the active principle and an appropriate solvent.

Administration by inhalation can be provided by using, e.g., an aerosol containing sorbitan trioleate or oleic acid, for example, together with trichlorofluoromethane, dichlorofluoromethane, dichlorotetrafluoroethane or any other biologically compatible propellant gas; it is also possible to use a system containing the active principle, by itself or associated with an excipient, in powder form.

The active principle can also be formulated as microcapsules or microspheres, e.g., liposomes, optionally with one or more carriers or additives.

Implants are among the prolonged release forms which can be used in the case of chronic treatments. They can be prepared in the form of an oily suspension or in the form of a suspension of microspheres in an isotonic medium.

The daily dose of a compound as described herein for treatment of a disease or condition cited above is about 0.001 to about 100 mg/kg of body weight per day, preferably about 0.001 to about 10 mg/kg. For an average body weight of 70 kg, the dosage level is therefore from about 0.1 to about 700 mg of drug per day, given in a single dose or 2–4 divided doses. It is contemplated that any range of the aforementioned doses may be administered at intervals greater than daily, e.g., one of four times per week over a period of several weeks or for greater periods. The exact dose, however, is determined by the attending clinician and is dependent on the potency of the compound administered, the age, weight, condition and response of the patient.

The therapeutically effective amount of the compounds of this invention that can be combined with the pharmaceutically acceptable carrier to produce a single dosage form will vary depending upon the age and condition of the host treated and the particular mode of administration. In general, the compounds of this invention are most desirably administered at a concentration level that will generally afford antiretrovirally effective results without causing any medically unacceptable harmful or deleterious side effects.

While the compounds of this invention can be administered as the sole active pharmaceutical agents, the compounds can also be used in combination with one or more other pharmaceutical agents which are not deleterious to the activity of the compounds of this invention or whose combination with the compounds will not have a deleterious effect on the host treated. Indeed, it is also contemplated that compounds of this invention may be combined with other antiviral agents or other agents useful in the treatment of conditions resulting from viral infection.

The following examples are provided to merely illustrate certain aspects of the present invention and should not be construed as a limitation thereof.

EXAMPLE 1

Preparation of 2-[[1-(5-amino-2-methylphenyl)ethyl]sulfonyl]-pyridine-N-oxide (Compound 1)

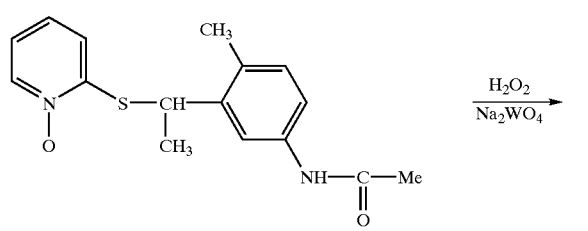

-continued

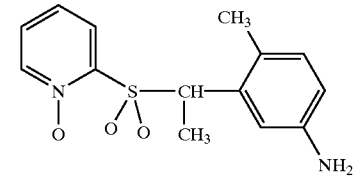

To a stirred room temperature solution of 3.0 g (0.01 mole) of 2-[[1-(5-acetylamino-2-methylphenyl)ethyl]thio]-pyridine-N-oxide in 10 ml of methanol were added 0.12 g of $Na_2WO_4$ followed by 1 g of 35% hydrogen peroxide added over 20 minutes. The exothermic reaction was cooled using a room temperature water bath. The mixture was stirred for 20 minutes, and then treated dropwise with another 1.3 g of 35% $H_2O_2$. The mixture was warmed to 35–43° C. for two hours, and then left to stir at room temperature overnight. The mixture was then treated with 5 ml of ethanol, 10 ml of water, and 5 ml of concentrated HCl and heated on a steam cone for one hour. The mixture was cooled, diluted with 20 ml of water and filtered to remove a solid. The filtrate was made basic with concentrated aqueous ammonium hydroxide to give a tacky solid. This solid was taken up in 30 ml of water and 3 ml of concentrated HCl and some insoluble material was filtered off. The filtrate was basified to give a solid precipitate that was filtered off, washed with water, and left to dry overnight. The dry solid weighed 0.85 g and melted at 165–170° C. Recrystallization gave a solid with a melting point of 184–188° C. and having infrared and NMR spectra consistent with the proposed structure.

EXAMPLE 2

Preparation of 1,4-xylyl-bis-2-sulfonyl pyridine-N-oxide (Compound 23)

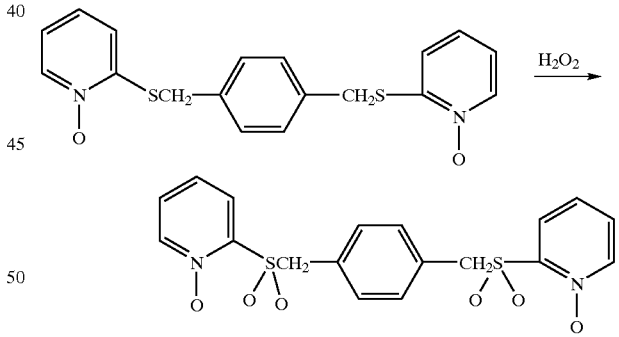

To a mixture of 14 g of 1,4-xylyl-bis-2-thio-pyridine-N-oxide in 175 ml of glacial acetic acid was added 20 ml of $H_2O_2$ (30% in water). The mixture was stirred over a weekend and then a further 8 ml of 30% $H_2O_2$ was added and the mixture was heated to 50–60° C. for 2 hours. The mixture was cooled and evaporated to dryness. Chloroform was then added and the mixture was brought to boiling and then cooled and let stand overnight. The insoluble product was filtered off, washed with ethanol, and then with chloroform. 13.6 g of final product was obtained, having a melting point of 233–235° C. Analysis calculated for $C_{18}H_{16}N_2S_2$: C=51.42; H=3.84; N=6.66. Found: C=47.39; H=4.10; N=6.74.

EXAMPLE 3

Preparation of 1,4[1,2,4,5-tetramethylbenzyl]-bis-(2'-sulfonylpyridine-N-oxide)

(Compound 25)

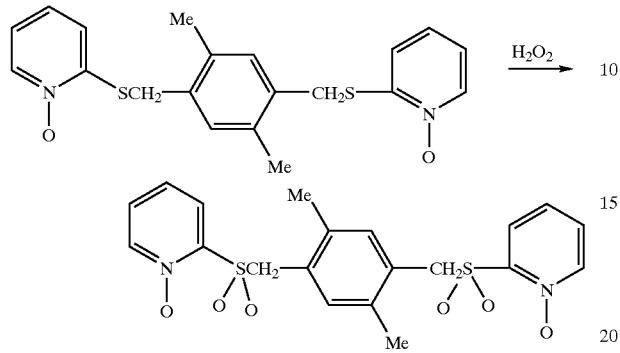

To a mixture of 1,4[1,2,4,5-Tetramethylbenzyl]-bis-(2'-thiopyridine-N-oxide) in 175 ml of glacial acetic acid was added 25 ml of 30% aqueous $H_2O_2$. The reaction mixture was allowed to stir overnight, then an additional 25 ml of 30% aqueous $H_2O_2$ was added, and the mixture was heated at 50–60° C. for 4 hours. Then, 600 ml of water and 100 g of ice was added. The white solid was filtered off and dried at room temperature, having a melting point of 242–244° C. Recovery was 2.2 g. An infrared spectrum was consistent with the structure.

EXAMPLE 4

Preparation of 2-(4'-tert-pentylphenylmethylsulfonyl) pyridine-N-oxide)

(Compound 40)

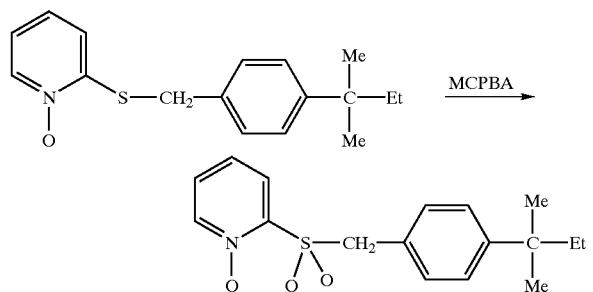

A mixture of 2.9 g (0.01 mole) of 2-(4'-t-pentylphenylmethylthio)pyridine-N-oxide) with 50 ml of chloroform and 80 ml of pH 7.5 phosphate buffer was maintained at 40° C. while 4 g (0.02 mole) of 85% metachloroperbenzoic acid (MCPBA) dissolved in 50 ml of chloroform was added. The mixture was stirred overnight, and the chloroform phase was then separated, washed with sodium bicarbonate, decanted and dried over anhydrous $Na_2SO_4$. The chloroform was filtered from the $Na_2SO_4$ and evaporated to leave 2.5 g of an oil which did not crystallize. An infrared spectrum was consistent with the structure.

EXAMPLE 5

Preparation of 2[1-(9-anthryl)methylsulfonyl] pyridine-N-oxide (Compound 51)

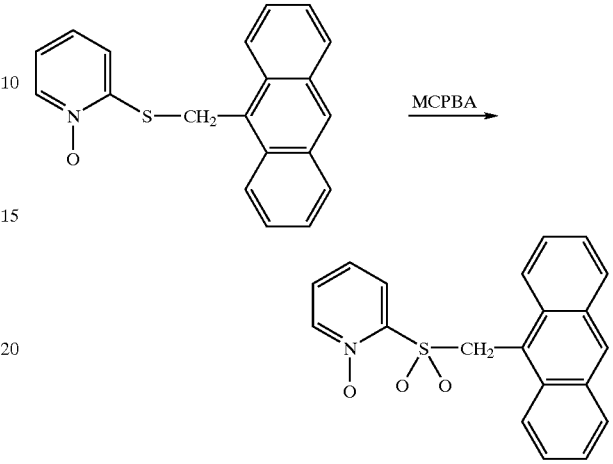

A mixture of 14.27 g (0.045 mole) of 2-[1-(9-anthryl) methylthio-pyridine-N-oxide in 250 ml of chloroform was cooled to 10° C. and stirred. Then 18 g (0.09 mole) of metachloroperbenzoic acid dissolved in 250 ml of chloroform was added slowly, and the reaction mixture was allowed to warm to room temperature and held at that temperature overnight. The reaction mixture was washed with $NaHCO_3$ solution in water, the chloroform layer was separated, and then dried with anhydrous sodium sulfate. The chloroform solution was filtered and the solvent removed. The residue was recrystallized from ethanol to give 10 g (66%) of a solid having a melting point of 213–215° C. Calculated for $C_{20}H_{15}N_3S$: C=68.76; H=4.33; N=4.01. Found: C=67.32; H=4.25; N=3.89.

EXAMPLE 6

Preparation of ethyl-N-[4-(pyridyl-N-oxide-2-sulfonylmethyl)phenylcarbonyl]carbamate (Compound 60)

To 5.86 g (0.020 mole) of 4[((1-oxo-2-pyridyl)sufonyl) methyl]benzoic acid in 50 ml of methylene chloride was added 2 g of triethylamine. The mixture was stirred at room temperature for 10 minutes and then 1.9 ml of $ClCO_2Et$ was added at 0° C., and the mixture was stirred at 0° C. for 30 minutes. To this mixture was added 1.78 g of urethane ($H_2NCO_2Et$) and the mixture was refluxed for 60 minutes.

The reaction mixture was evaporated under reduced pressure, dissolved in ethanol, and poured into water. The solid was filtered off, washed with ether, and air-dried to give 2 g of product having a melting point of 90–92° C. An NMR spectrum was consistent with the structure.

EXAMPLE 7

Preparation of 2-[(3-methoxy-4-benzyloxy)phenylmethylsulfonyl]pyridine-N-oxide (Compound 61)

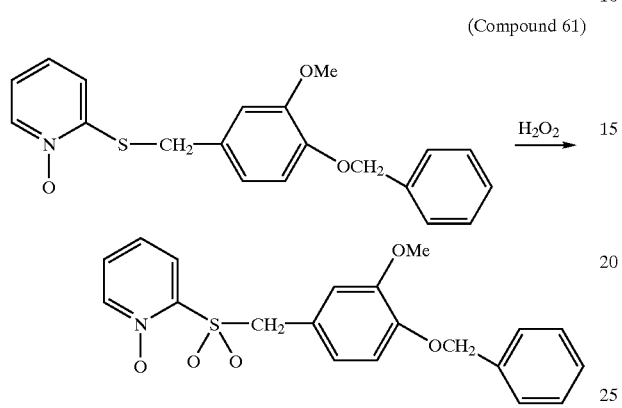

A mixture of 6.0 g (0.017 mole) of 2-[(3-Methoxy-4-benzyloxy) phenylmethylthio]-pyridine-N-oxide, 0.02 g of $Na_2WO_4$ and 10 ml of glacial acid was prepared and brought to 40° C. To the above mixture was added 4.25 ml (0.017 mole) of 35% hydrogen peroxide. The whole mixture was then brought to 85° C. for one hour, cooled and then poured into ice water. The solid product was filtered off and dried to give 7.1 g of crude material. This crude material was recrystallized from ethanol to give 3.0 g of pure product having a melting point of 137–139° C.

EXAMPLE 8

Preparation of 2-[[(2-nitro-5-methylphenyl)methyl]sulfonyl]pyridine-N-oxide (Compound 62)

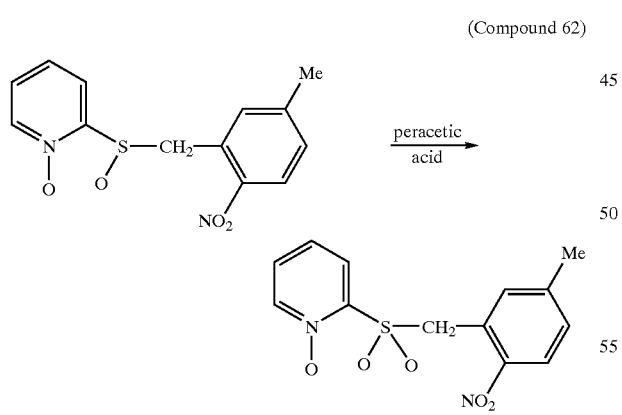

Five grams [5.0 g (0.02 mole)] of 2-[[(5-Methyl-2-nitrophenyl) methyl]sulfinyl]pyridine-N-oxide, was slurried in 30 ml of glacial acetic acid. The slurry was stirred while 3.6 g of 40% peracetic acid (1.11 mole) was added dropwise. After addition, the mixture was heated to 60° C. for 4 hours, allowed to cool and stirred at room temperature overnight. Excess peracetic acid was destroyed using $NaHSO_3$. The mixture was neutralized with $K_2CO_3$ solution, and the solid was filtered and washed with water. After drying, the solid melted at 178–183° C. and had an NMR consistent with the proposed structure.

EXAMPLE 9

Preparation of 2[[[2,5-bis-(1-methylethyl)-4-bromophenyl]methyl] sulfonyl]pyridine-N-oxide (Compound 63)

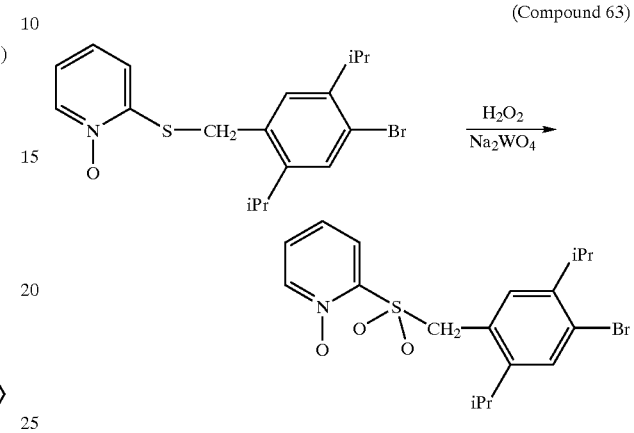

A solution of aqueous hydrogen peroxide (1.6 g) was added dropwise to a mixture of 3.0 g (0.0079 mole) of 2[[[2,5-bis-(1-Methylethyl)-4-bromophenyl]-methyl]thio]-pyridine-N-oxide, 50 ml of methanol, and 0.1 g of $Na_2WO_4$. The suspension was heated at reflux for 2 hours and everything dissolved. About 25 ml of methanol was removed from the mixture, and the remaining solution was allowed to crystallize at room temperature. The crystalline material, having a melting point of 161–175° C., was filtered off and recrystallized from methanol with a resulting melting point of 171–174° C. The infrared and NMR spectra were consistent with the proposed structure.

EXAMPLE 10

Preparation of 2-[[(3-nitro-4-chlorophenyl)methyl]sulfonyl]pyridine-N-oxide (Compound 64)

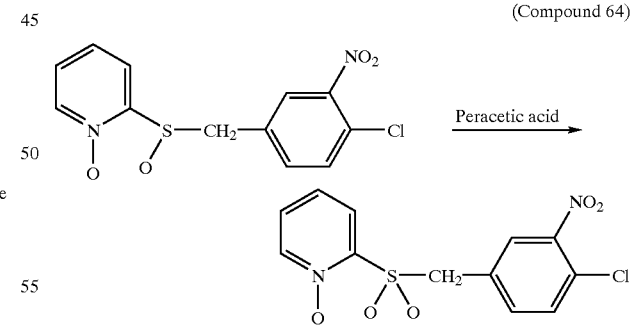

To a mixture of 14.0 g (0.0426 mole) of 2-[[(4-chloro-3-nitrophenyl) methyl]sulfinyl]-pyridine-N-oxide in 35 ml of acetic acid was added 10.1 g of peracetic acid (40% in acetic acid) dropwise over one hour. The temperature of the reaction mixture rose to 27° C. before a water bath was placed on the flask to hold the temperature at 25° C. After addition, the mixture was heated to 70° C. for five hours. The mixture was cooled, and 20 ml additional acetic acid and solid sodium bisulfate and water were added to destroy the excess peracetic acid. The aqueous mixture was neutralized with potassium carbonate and chilled in an ice bath to precipitate an almost white solid. This solid was filtered off, washed with water, dried under vacuum overnight, and had a melting point of 162–164° C. Infrared and NMR spectra were both consistent with the proposed structure. The product was recrystallized from ethanol to give needle-like white crystals having a melting point of 168–170° C. C,H,N calculated for $C_{12}H_9ClN_2O_5S$: C=43.85%; H=2.76%; N=8.52%. Found: C=43.27% H=2.65%; N=8.21%.

EXAMPLE 11

Preparation of 2-[[(3,5-dinitrophenyl)methyl]sulfonyl]pyridine-N-oxide (Compound 65)

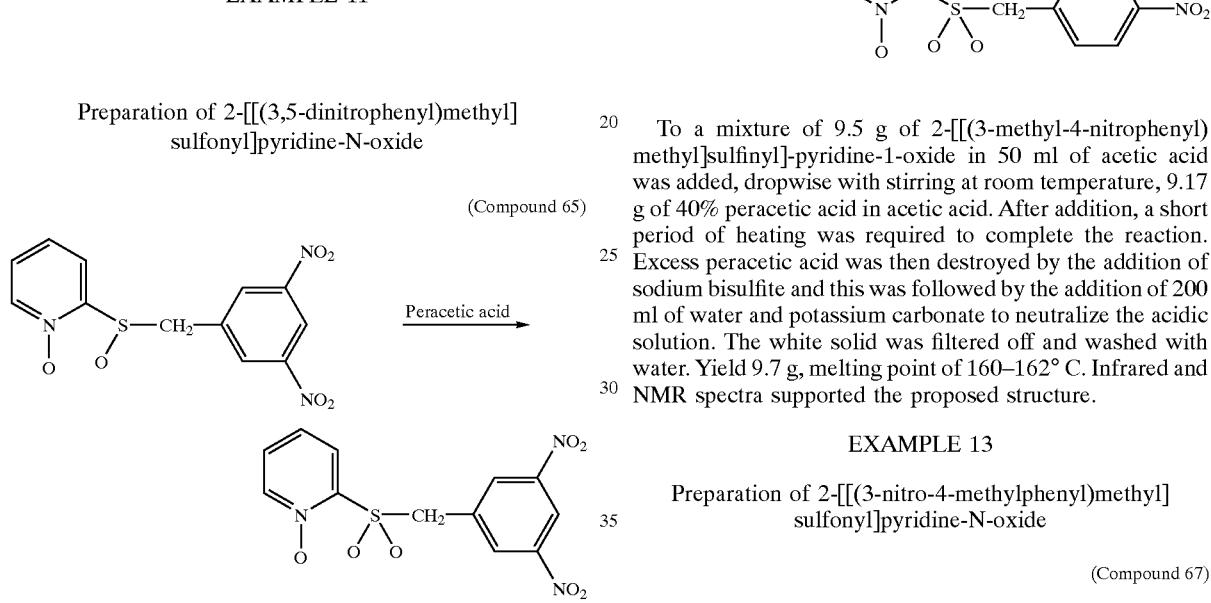

To 14.0 g (0.043 mole) of 2-[[(3,5-dinitrophenyl)methyl]sulfinyl]-pyridine-N-oxide in 35 ml of glacial acetic acid was added, dropwise over 0.5 hours with stirring, 8.2 g of 40% peracetic acid in acetic acid. After addition was complete, the mixture was heated to 70° C. for 4.5 hours. The mixture was cooled to room temperature, and then an additional 2.0 g of 40% peracetic acid was added, and the mixture heated to 45–50° C. for three hours while stirring. The mixture became quite thick, so 20 ml of glacial acetic acid was added to enable better stirring and heating was continued at 70° C. for one more hour, followed by stirring at 30° C. overnight. Workup of a small aliquot indicated some sulfoxide to still be present, so heating was continued at 65–70° C. for 4 more hours. The excess peracetic acid was then destroyed by adding 100 ml of water and sodium bisulfite. After neutralizing the mixture to pH 4 with potassium carbonate, the white solid was filtered off, and then dried under vacuum. Yield was 11.5 g or 79%, having a melting point of 198–201° C. This material was recrystallized from ethanol to give a white solid, melting point 202–204° C. Infrared and NMR spectra were consistent with the proposed structure.

EXAMPLE 12

Preparation of 2-[[(3-methyl-4-nitrophenyl)methyl]sulfonyl]pyridine-N-oxide (Compound 66)

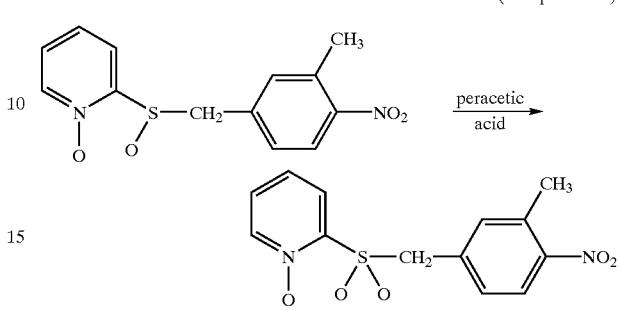

To a mixture of 9.5 g of 2-[[(3-methyl-4-nitrophenyl)methyl]sulfinyl]-pyridine-1-oxide in 50 ml of acetic acid was added, dropwise with stirring at room temperature, 9.17 g of 40% peracetic acid in acetic acid. After addition, a short period of heating was required to complete the reaction. Excess peracetic acid was then destroyed by the addition of sodium bisulfite and this was followed by the addition of 200 ml of water and potassium carbonate to neutralize the acidic solution. The white solid was filtered off and washed with water. Yield 9.7 g, melting point of 160–162° C. Infrared and NMR spectra supported the proposed structure.

EXAMPLE 13

Preparation of 2-[[(3-nitro-4-methylphenyl)methyl]sulfonyl]pyridine-N-oxide (Compound 67)

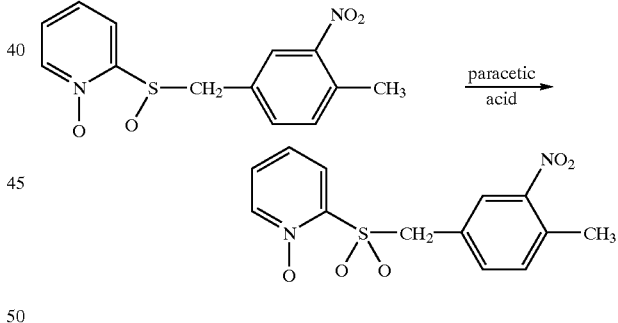

To a mixture of 12.1 g (0.042 mole) 2-[[(4-methyl-3-nitrophenyl)methyl]sulfinyl]-pyridine-1-oxide in 35 ml of acetic acid was added, dropwise at room temperature over one-half hour, a solution of 9.2 g (1. 16 mole) of 40% peracetic acid in acetic acid. The reaction mixture was heated to 70° C. for two hours, and then allowed to cool and stir at room temperature overnight. An additional period of heating at 70° C. for five hours was instituted after which time work-up of a small portion of the mixture indicated some starting material to still be present. Heating and stirring at 70° C. for two more hours, and then standing at room temperature over the weekend completed the reaction. Excess peracetic acid was then destroyed with sodium bisulfite followed by the addition of 100 ml of water and neutralization with potassium carbonate. The aqueous mixture was chilled in an ice bath to precipitate yellow/white crystals. These were filtered off, washed with water and dried. Recrystallization from ethanol gave 2.9 g of white fluffy needles, having a melting point of 154–156° C. Infrared and NMR spectra were in agreement with the proposed structure.

EXAMPLE 14

Preparation of 2-[[(2-chloro-4-nitrophenyl)methyl]sulfonyl]pyridine-N-oxide (Compound 69)

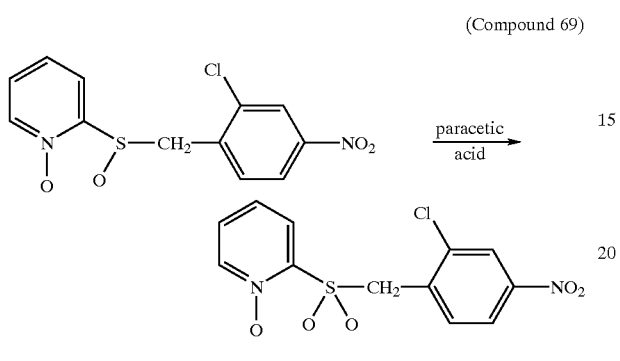

To a mixture consisting of 16.1 g (0.055 mole) of 2-[[(2-chloro-4-nitrophenyl)-methyl]sulfinyl]-pyridin-1-oxide and 60 ml of acetic acid was added, dropwise at room temperature over 0.5 hours, 13.5 g (1.3 mole) of peracetic acid in acetic acid (40%). The mixture was heated at 70° C. for six hours. The reaction was worked up in the usual fashion, but the product proved to be a mixture of the starting material and desired sulfone. The isolated material (10 g), estimated to contain about 16% sulfoxide, was subsequently redissolved in 40 ml of acetic acid and 1.33 g of 40% peracetic acid in acetic acid was added. The mixture was heated for seven hours at 70° C. and then stirred at room temperature overnight. The excess peracetic acid was destroyed with sodium bisulfite, the mixture was then poured into ice water and then neutralized with potassium carbonate. The solid was filtered off and dried, having a melting point of 199–201° C. An NMR spectrum supported the proposed structure.

EXAMPLE 15

Preparation of 2-[(2,5-dimethylphenyl)chloromethylsulfonyl]-6-methylpyridine-N-oxide a) Preparation of 2-[(2,5-dimethylphenyl)methylthio]-6-methylpyridine-1-oxide

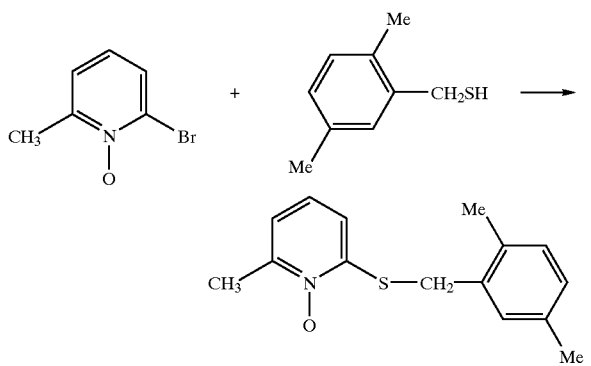

A mixture of 4.48 g (0.020 mole) of 2-bromo-6-methylpyridine hydrochloride, 3.34 g (0.022 mole) of 2,5-dimethylbenzylmercaptan and 0.88 g (0.022 mole) of powdered sodium hydroxide were stirred together at room temperature in 35 ml of DMF for 3.5 hours. The reaction mixture was poured into water and the precipitate filtered off and washed with water. Yield 1.96 g or 38%.

b) Preparation of 2-[(2,5-dimethylphenyl)methylsulfonyl]-6-methylpyridine-1-oxide

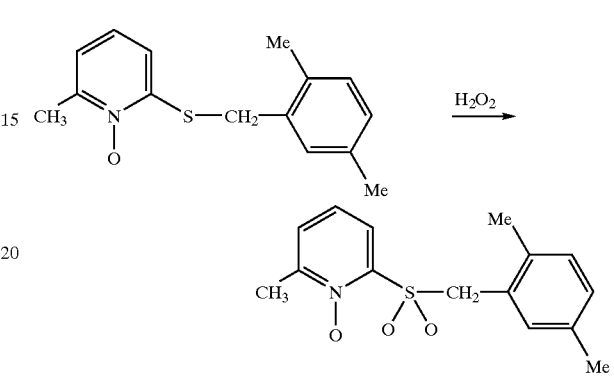

The sulfide isolated in step (a) above was dissolved in 15 ml of glacial acetic acid and then 2 ml of 30% hydrogen peroxide was added along with 50 mg of sodium tungstate. The reaction mixture was heated at 40° C. for two hours, cooled, and poured into water to percipitate the product. Yield, 1.53 g.

c) Preparation of 2[(2,5-dimethylphenyl)chloromethylsulfonyl]-6-methylpyridine-N-oxide (Compound 73)

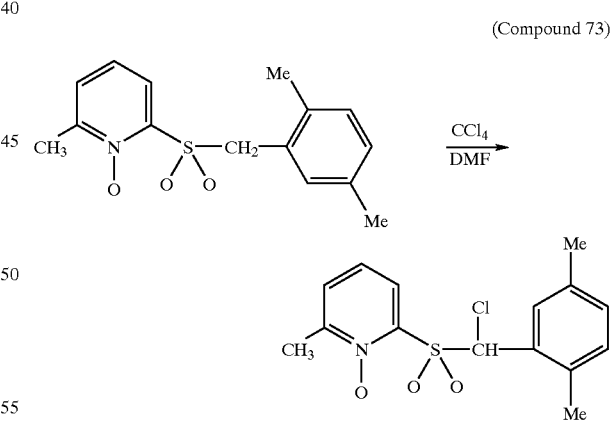

The sulfone (1.53 g or 0.0053 mole) prepared in step (b) above, was added to a mixture of 0.24 g (0.006 mole) of NaOH, 1.1 g (0.007 mole) of carbon tetrachloride and 15 ml of DMF at −10–0° C. After 30 minutes of stirring, the reaction mixture was quenched with water and the precipitate was filtered off, washed with water, and dried. Yield 1.67 g, melting point 177° C., with decomposition. An NMR spectrum supported the proposed structure.

EXAMPLE 16

Preparation of 2-[1-(2,5-dimethylphenyl)ethylsulfonyl]-6-chloropyridine-N-oxide (Compound 76)

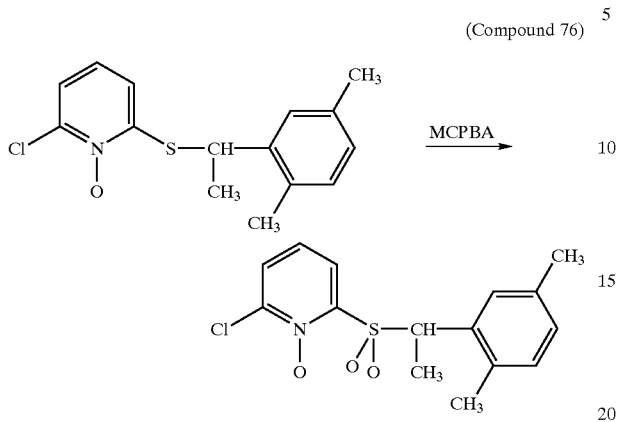

To a stirred and cooled solution of 5.44 g (0.018 mole) of 2-[1-(2,5-dimethylphenyl)ethylthio]-6-chloropyridine-N-oxide in 100 ml of chloroform was added 12 g (0.05 mole) of metachloroperbenzoic acid in 150 ml of chloroform. The reaction mixture was kept cold in a refrigerator for one day. The precipitated metachlorobenzoic acid was removed and the reaction mixture was washed with sodium bicarbonate, and then water. The chloroform phase was dried, and the chloroform then removed using a vacuum. The solid product (5.0 g) had a melting point of 190° C. to 198° C. which was recrystallized from ethanol/ethyl acetate (95/5) to give 3.2 g (55%) of product. Melting point was 197–200° C. Analysis for $C_{15}H_{16}NO_3SCl$ Calc: C=55.27, H=4.95, N=4.30, S=9.84, Cl=10.88. Found: C=55.20, H=4.95, N=3.98, S=9.47, Cl=10.83.

EXAMPLE 17

Preparation of 2-(2,5-dimethylphenylmethylsulfonyl)-6-chloropyridine-N-oxide

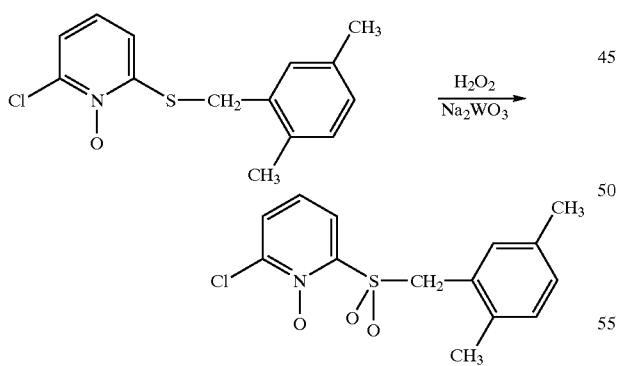

To a stirred solution of 3.5 g (0.01 25mole) of 2-(2,5-dimethylphenyl)-methylthio)-6-chloropyridine-N-oxide in 75 ml of acetic acid was added 150 mg of sodium tungstate and then 10 g of 30% hydrogen peroxide over a period of 10 minutes. The reaction mixture was heated at 45° C. for 2 hours and allowed to stand overnight. The solid product was recrystallized from ethanol/water (75/25). Melting point was 208 to 209° C. The product showed JR bands at 1340 and 1180 cm-1 ascribed to $SO_2$.

EXAMPLE 18

Preparation of 2-[1-(2,5-dimethylphenyl)ethylsulfonyl]-4,6-dimethylpyridine-N-oxide (Compound 81)

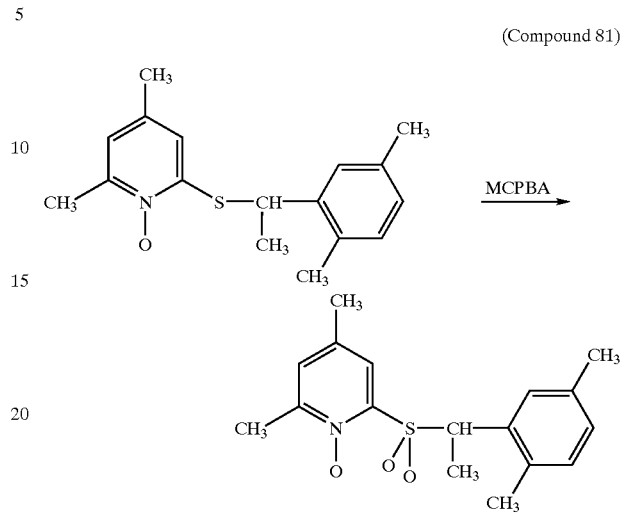

To a stirred and cooled solution of 2.88 g (0.01 mole) of 2-(1-(2,5-dimethylphenyl)ethylthio]-4,6-dimethylpyridine-N-oxide in 50 ml of chloroform was added 7.5 g (0.043 mole) of 80% active metachloroperbenzoic acid. The reaction mixture was kept cold in a refrigerator for 2 days. The precipitated metachlorobenzoic acid was removed and the reaction mixture was washed with sodium bicarbonate, and then water. The chloroform phase was dried, and the chloroform then removed using vacuum. The solid product (3.0 g or 98%) was recrystallized from ethanol/water. Melting point was 201–204° C. Analysis for $C_{17}H_{21}SO_3N$ Calc: C=64.08,H=6.62, N=4.38, S=10.03 Found: C=62.53,H= 7.09, N=4.16,S=9.64.

EXAMPLE 19

Preparation of 2-[(2,5-dimethylphenyl)chloromethylsulfonyl]pyridine (Compound 106)

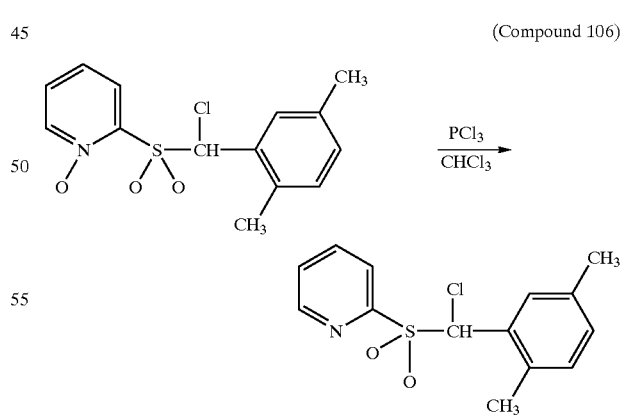

A mixture of 2.0 g (0.0064 mole) of 2-[(2,5-dimethylphenyl)-chloromethylsulfonyl]-pyridine N-oxide, 3.5 g (0.026 mole) of $PCl_3$ and 15 ml of chloroform was refluxed for one hour. Addition of ethanol to destroy excess $PCl_3$ and evaporation of the solvents left 2.6 g of crude product. The crude material was recrystallized from ethanol to give 1.5 g (79%) of crystalline material having a melting point of 117–119° C. Infrared and NMR spectra were in agreement with the structure. Analysis calculated for $C_{14}H_{14}ClNO_2S$: C=56.85; H=4.77; N=4.74. Found: C=56.67; H=4.78; N=4.81.

EXAMPLE 20

Preparation of 8-ethyl-4-methyl-2-[(1-phenylethyl)sulfonyl]-quinoline

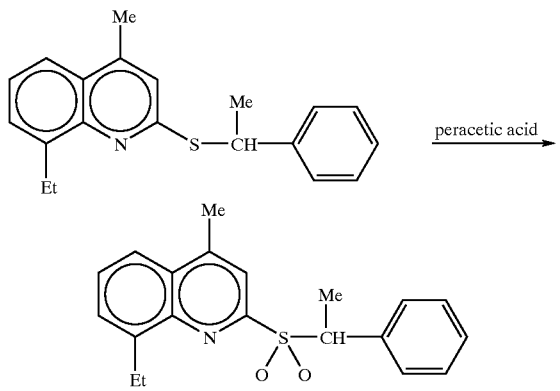

To a mixture of 4.5 g of 8-ethyl-4-methyl-2-[(1-phenylethyl)thio]-quinoline in 40 ml of acetic acid was added slowly 17.3 g of 40% peracetic acid in acetic acid. The mixture was stirred for three hours in an ice bath, brought to room temperature, and then stirred at room temperature overnight. A white precipitate formed, which was filtered off and recrystallized from ethanol, having a melting point of 146.5–147.5° C. Yield was 2.7 g. An NMR spectrum supported the structure. C,H,N,S calculated for $C_{22}H_{25}NO_2S$: Theoretical: C=71.91; H=6.86; N=3.81; S=8.73; Found: C=71.73; H=7.00; N=3.53; S=6.46.

EXAMPLE 21

Preparation of 2-[[1-(2,5-dimethylphenyl)-2-methoxyethyl]sulfonyl]pyridine (Compound 123)

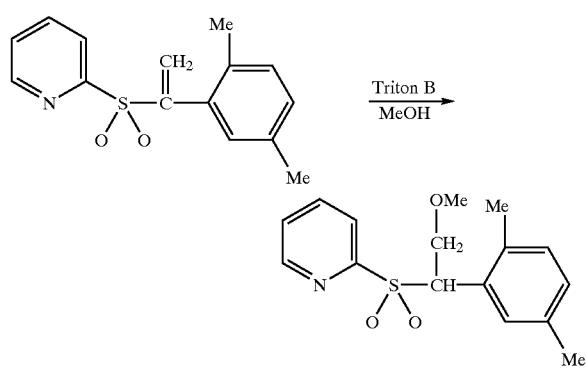

The starting material (0.1 g) was placed in 2 ml of methanol and 10 drops of 40% Triton B were added. The mixture was heated at 40° C. for two hours, and the methanol was then allowed to evaporate. An NMR spectrum was consistent with the proposed structure, and the compound had a melting point of 91–93° C.

EXAMPLE 22

Preparation of 3-chloro-2-[[1-(2,5-dimethylphenyl)ethyl]sulfonyl]pyridine-N-oxide (Compound 124)

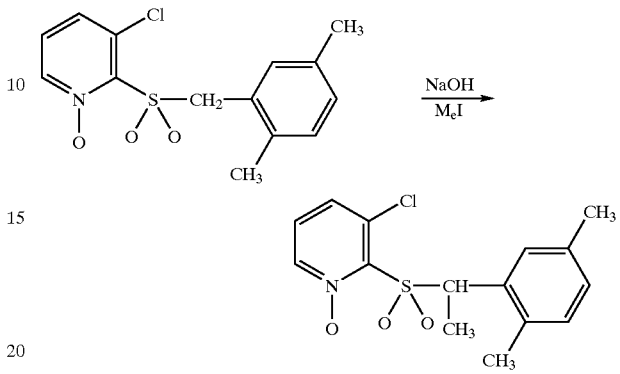

A solution 3.0 grams of 3-chloro-2-[[1-(2,5-dimethylphenyl)methyl]sulfonyl pyridine-N-oxide in 15 ml of dimethylformamide was cooled to 5° C. and then treated with 0.5 g of NaOH. The mixture was stirred for five minutes and then 0.75 ml of methyl iodide was added. The mixture was stirred for two more hours, and then allowed to stand overnight. Cold water was added to precipitate the product. The solid was filtered off, washed with water and dried, yield 2.4 g, melting point of 148–1 54° C. An infrared spectrum and the elemental analysis for CH&N confirmed the structure.

EXAMPLE 23

Preparation of 3-chloro-2-[[chloro(2,5-dimethylphenyl)methyl]sulfonyl]pyridine-N-oxide (Compound 125)

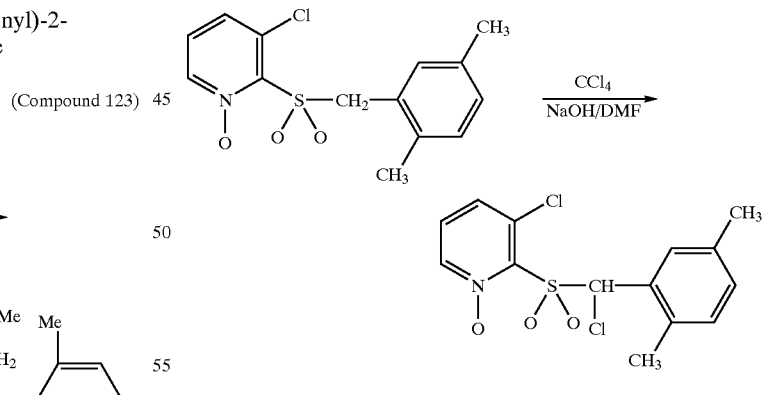

To a suspension of 2.2 g (0.01 mole) of 3-chloro-2-[[1-(2,5-dimethylphenyl)-methyl]sulfonyl]pyridine-N-oxide in 10 ml of dimethylformamide (DMF) was added 2 g (0.013 mole) of carbon tetrachloride. The mixture was cooled to 15° C. and then treated with 0.5 g (0.013 mole) of NaOFl. The mixture was stirred and allowed to warm to room temperature for two hours. It was then poured into cold water and the solid was filtered off, having a melting point of 125–127° C. Infrared and NMR spectra were consistent with the proposed structure.

EXAMPLE 24

Preparation of 3-chloro-2-[(phenylmethyl)thio]pyridine-N-oxide (Compound 132)

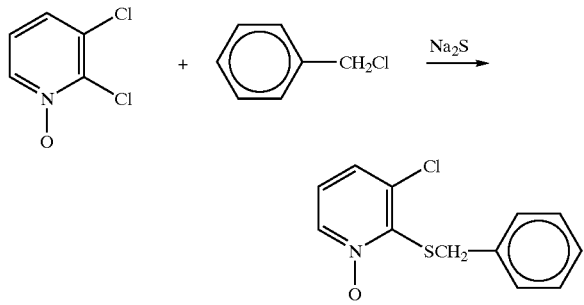

A mixture of 5 g of 2,3-dichloropyridine-N-oxide, 4 g of sodium sulfide, and 30 ml of water was heated to 70° C. for three hours. The mixture was cooled and then 3.8 g of benzyl chloride was added dropwise. The resulting mixture was heated to 70° C. for four hours and then cooled and extracted with toluene. The toluene solution was dried with $Na_2SO_4$ and the toluene then removed. 10 ml of toluene was then added back and the crystalline precipitate was filtered off and washed with 5 ml of cold toluene. 1.4 g of white crystals were obtained, having a melting point of 70–73° C. The elemental analysis for CH&N, the infrared spectrum and the NMR spectrum were all consistent with the proposed structure. A second (1.8 g) and third (0.1 g) crop could be obtained from the toluene mother liquors and these crops were recrystallized from ether to give a further 1.5 g of pure material having a melting point of 70–74° C.

EXAMPLE 25

Preparation of 3-chloro-2-[[(2,5-dimethylphenyl)methyl]thio]pyridine-N-oxide (Compound 133)

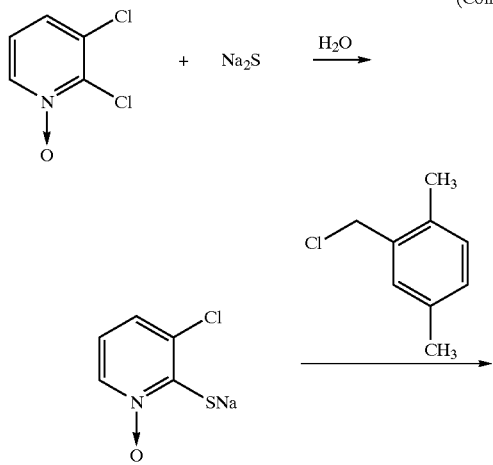

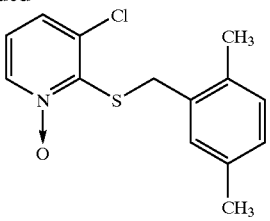

2,3-Dichloropyridine N-oxide (4.3 g, 0.026 mole) (prepared according to U.S. Pat. No. 3,850,939) and sodium sulfide (3.4 g, 0.026 mole) were mixed with 25 mL of water and then heated to 70 degrees for two hours. The resulting mixture was cooled to room temperature and treated with 2,5-dimethylbenzyl chloride (4.3 g, 0.026 mole) drop wise. After the addition, the mixture was heated to 70 degrees for four hours, then cooled in an ice bath. The precipitated solid was filtered and washed with cold toluene leaving 3.5 g of product. Recrystallization from toluene afforded pure product having a melting point of 77–80° C. The compound was identified by its NMR spectrum. NMR data ($CDCl_3$): 2.3 (s, 6H); 4.5 (s, 2H); 7.1–8.0 (m, 6H).

EXAMPLE 26

Preparation of 4-(1,1-dimethylethyl)-2-[(4-methoxyphenyl)methylthio]pyridine-N-oxide (Compound 134)

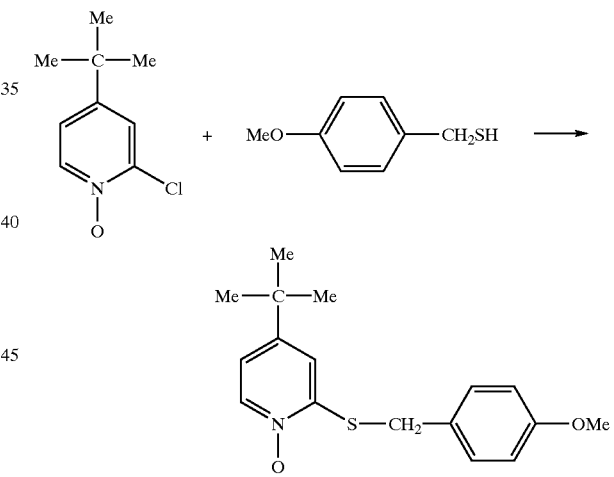

Under nitrogen, to a solution of 10 g (0.065 mole) of 4-methoxybenzyl ercaptan in 50 ml of methanol were added 2.6 g of NaOH dissolved in 5 ml of water and 40 ml of methanol. To the above mixture was slowly added 12 g (0.065 mole) of 2-chloro-4-t-butylpyridine-N-oxide dissolved in 50 ml of methanol. The mixture was refluxed under nitrogen with stirring for about 3 hours, and then allowed to stir at room temperature overnight. Then 400 ml of water was added and the mixture was stirred and warmed slightly to digest. Saturated NaCl solution and chloroform (400 ml) was added and the phases separated. The chloroform layer was washed with 400 ml of water, dried over $Na_2SO_4$, filtered, and the chloroform removed on a rotovap to leave an amber viscous oil, which slowly crystallized. This was taken up in petroleum ether, filtered and dried, to give 8.7 g of crude product having a melting point of 134–143° C. It was recrystallized from 125 ml of ethyl acetate to give 5.4 g of a white crystalline solid having a melting point of 144.5–146° C. The infrared and NMR spectra were consistent with the structure.

EXAMPLE 27

Preparation of 3-chloro-2-[(phenylmethyl)sulfinyl] pyridine-N-oxide (Compound 136)

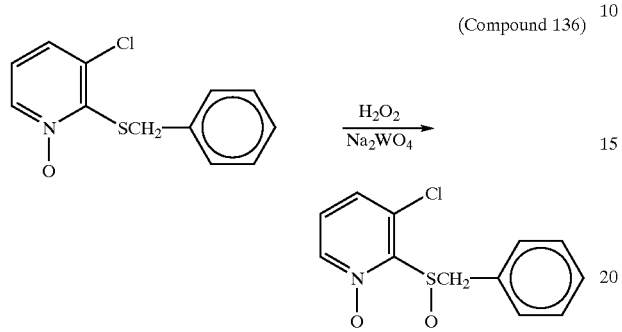

To 4.7 g of the starting sulfide (See Example 24 above) dissolved in 25 ml of methanol were added a pinch of $Na_2WO_4$ followed by 1.5 g of 50% aqueous hydrogren peroxide. The mixture was stirred at room temperature for four hours, filtered, and the solid was washed with $NaHSO_3$ solution, followed by water. The dried solid 2.2 g, melting point of 119–122° C., gave an NMR which indicated mostly the desired sulfoxide but some contamination by the sulfone and sulfide. A second crop of 1.1 g, melting point 118–123° C., was also obtained. Attempts to recrystallize from toluene and from ethyl acetate gave material still contaminated by sulfone, so the mixture was finally separated by preparative HPLC and then recrystallized from ethyl acetate, having a melting point of 124–126° C. The elemental analysis for C,N&N, the infrared spectrum, and the NMR spectrum were all consistent with the proposed structure.

EXAMPLE 28

Preparation of 2-[[(2,6-dichlorophenyl)methyl]thio]-3-methyl-pyridine-N-oxide (Compound 137)

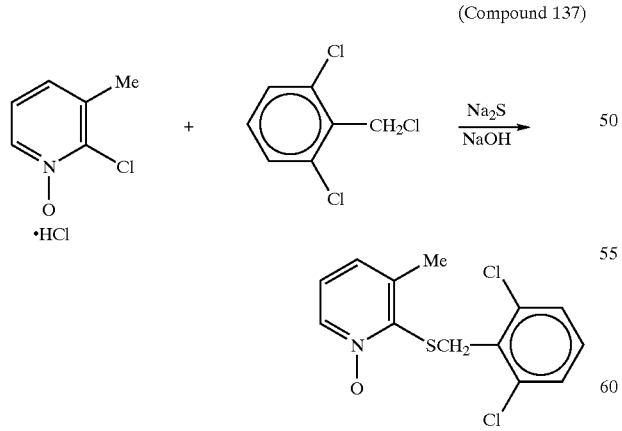

A solution consisting of 8.0 g of $Na_2S$ and 2.8 g of NaOH in 100 ml of water was treated with 10.8 g of 2-chloro-3-methylpyridine-N-oxide. The mixture was heated at 80° C. for three hours, cooled to room temperature, and then treated dropwise with 12.0 g of 2,6-dichlorobenzylchloride. The reaction mixture was heated back to 80° C. for three more hours, and then allowed to stand at room temperature overnight. The mixture was then extracted with two 200 ml portions of methylenechloride. The methylenechloride phases were dried, and solvent then removed to give a solid. The solid was taken up in ether and filtered to give 6.6 g of material having a melting point of 85–90° C. An NMR suggested a mixture of the desired product and the disulfide of the 3-methylpridine-N-oxide starting material. The mixture was separated with a preparative HPLC silica column and ethyl acetate as eluant. The desired product had a melting point 135–138° C., and NMR and infrared spectra supported the proposed structure.

EXAMPLE 29

Preparation of 2-[[(2,6-dichlorophenyl)methyl] sulfinyl]-3-methyl-pyridine-N-oxide (Compound 138)

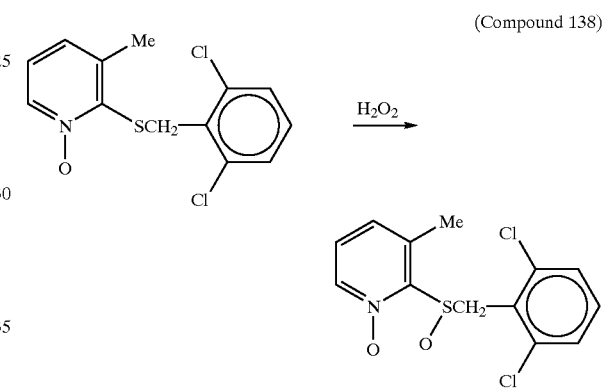

To 10.5 g (0.035 mole) of 2-[(2,6-dichlorophenyl) methylthio]-3-methyl-pyridine-N-oxide (See Example 28 above) dissolved in 100 ml of methanol were added a pinch of sodium tungstate and then dropwise 4.2 ml (0.4 mole) of 50% hydrogen peroxide. The temperature was maintained at 25° C. for four hours, and then a cold solution of $NaHSO_3$ was added slowly to destroy residual $H_2O_2$. The solid was filtered and air-dried, having a melting point of 178–181° C., yield 10 g. The elemental analysis for C,H,N; the infrared spectrum, and the NMR spectrum all supported the proposed structure.

EXAMPLE 30

Preparation of 2-[[(2,6-dichlorophenyl)methyl] sulfonyl]-3-methyl-pyridine-N-oxide (Compound 139)

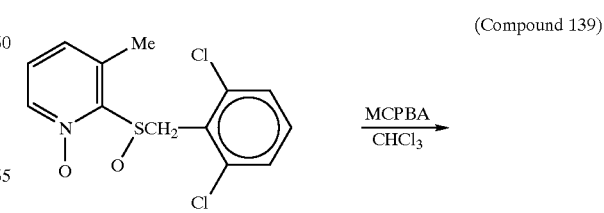

-continued

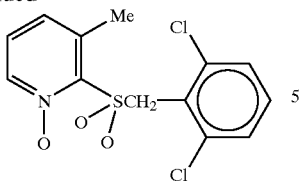

To 8.0 g (0.03 mole) of 2[(2,6-dichlorophenyl)methylsulfinyl]-3-methyl-pyridine-N-oxide (See Example 29 above) in 150 ml of chloroform were added 10 g (0.05 mole) of metachloroperbenzoic acid. The mixture was stirred at room temperature for 24 hours, and then was washed with 20% $K_2CO_3$, and then with aqueous $NaHSO_3$ until no peroxides were present. The chloroform layer was dried with $Na_2SO_4$ and then the mixture was filtered and the solvent removed on a steam bath. The residue was taken up in ether and filtered to give 2 g of solid, having a melting point of 215–218° C. The elemental analysis for C,H,N; the infrared, and the NMR all supported the proposed structure.

EXAMPLE 31

Preparation of 2-[[(2,5-dimethylphenyl)methyl]thio]-1-methyl-pyridinium chloride (Compound 142)

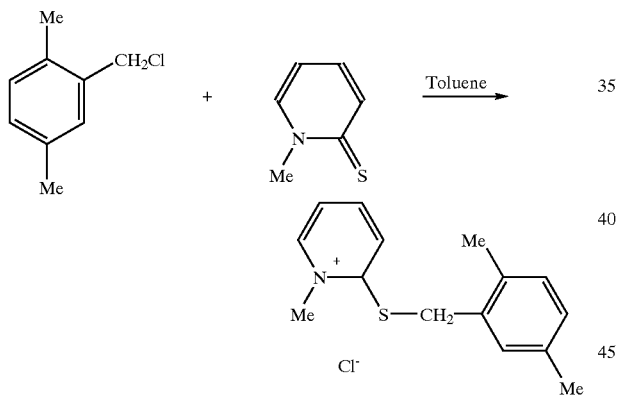

A mixture of 5.0 g of 1-methyl-2(1H)-pyridinethione and 6.2 g of 2,5-dimethylbenzyl-chloride in 40 ml of toluene was heated for five hours at 70° C. A pale yellow solid was filtered from the cooled mixture. Yield was 5 g having a melting point of 130–137° C. NMR and infrared spectra were consistent with the structure.

EXAMPLE 32

Preparation of 2-benzylthio-3-nitropyridine (Compound 146)

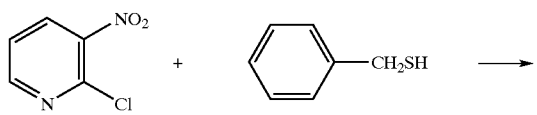

-continued

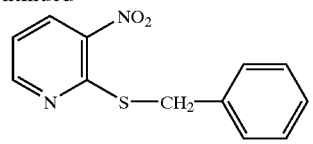

To a stirred solution of 35 ml of ethanol, 1 ml of water, and 2.0 g (0.025 mole) of 85% KOH pellets was added 3.2 g (0.025 mole) of benzyl mercaptan. To this mixture was added 4 g (0.025 mole) of 2-chloro-3-nitropyridine. After complete addition (20 minutes), the reaction mixture was warmed to 55° C. and held at that temperature for 25 minutes. It was then allowed to cool to room temperature over the next hour. The solid was filtered off (KCl) and the ethanol was removed from the filtrate. The residue was treated with 40 ml of acetone by warming, cooling and then filtering to remove more KCl. The filtrate was evaporated to leave an oil which solidified. The solid was recrystallized from 40 ml of ethanol to give 2.3 g of crystals, having a melting point of 57–59° C. The infrared spectrum was consistent with the structure. A second crop of 1.3 g of impure product was also obtained.

EXAMPLE 33

Preparation of 2-((2,5-dimethylphenyl)methylthio) pyridine (Compound 148)

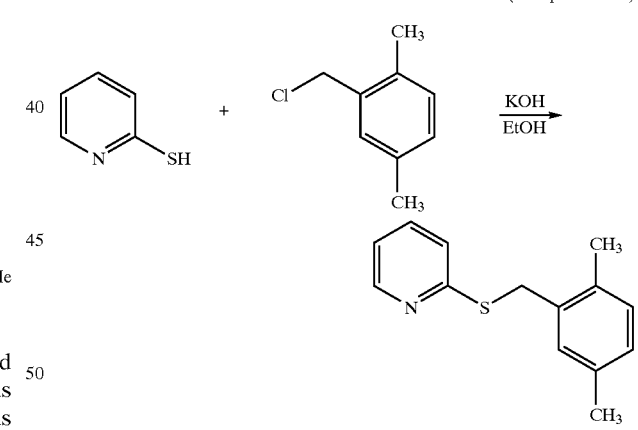

A mixture of 5.6 g (0.05 mole) of 2-mercaptopyridine, 3.3 g (0.05 mole) of potassium hydroxide (85% pellets), 35 ml of ethanol and 5 ml of water was prepared. To this mixture was added 7.8 g (0.05 mole) of 2,5-dimethyl-benzylchloride, while maintaining good stirring. The mixture was stirred and heated to 40° C. for 45 minutes, cooled to room temperature, and then added to 150 ml of water. The aqueous mixture was extracted with 150 ml of diethyl ether; the ether phase washed with 150 ml of water. Finally, the ether phase was dried with anhydrous sodium sulfate. Removal of the ether left a green oil. An infrared spectrum was consistent with the structure of 2-((2,5-dimethylphenyl)methylthio) pyridine.

EXAMPLE 34

Preparation of 6-chloro-(2-benzylthio)pyridine-N-oxide (Compound 149)

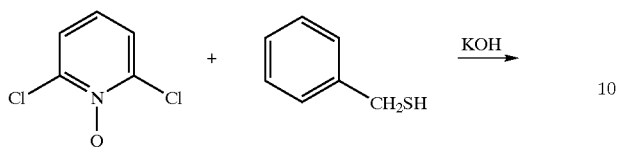

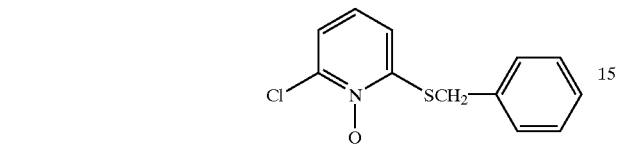

A solution of 2 g (0.03 mole) of KOH in 50 ml of ethanol and 0.5 ml of water was prepared. To this solution was added a mixture of 5 g (0.03mole) of 2,6-dichloropyridine-N-oxide and 3.8 g (0.03 mole) of benzylmercaptan. The resulting mixture was stirred and heated for 2 hours, and then evaporated to dryness. The residue was treated with 100 ml of chloroform and the insoluble portion (KCl) was filtered off. The chloroform was dried with sodium sulfate, filtered, and evaporated to dryness to leave a white solid having a melting point of 78 to 90° C. This solid was recrystallized from ethyl acetate, to give 5.8 g (77%) of product having a melting point of 112–115° C. Analysis calculated for $C_{12}H_{10}NSClO$: C=57.26, H=4.00, N=5.57. Found: C=57.03, H=3.00, N=4.32.

EXAMPLE 35

Preparation of 2-(2,5-dimethylbenzylsulfonyl)pyridine (Compound 150)

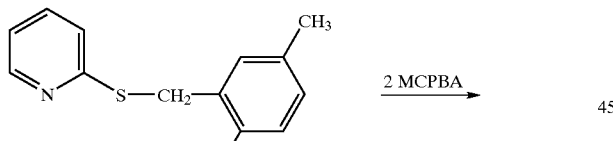

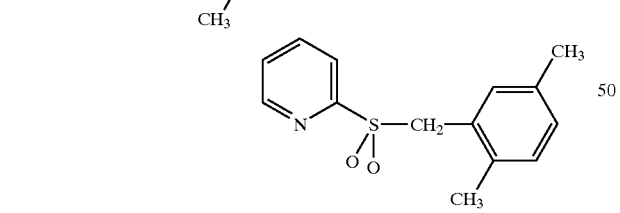

To a well-stirred and cooled (−10° C.) solution of 6.9 g (0.03 mole) of 2-(2,5-dimethyl-benzylthio)pyridine in 75 ml of chloroform was added portion-wise a solution of 12 g (0.06 mole) of metachloroperbenzoic acid dissolved in 100 ml of chloroform. The mixture was kept at −10° C. for 10 minutes and then allowed to warm to room temperature over the next six hours. It was stirred at room temperature overnight. Water was then added and the phases separated. he chloroform phase was washed with aqueous sodium bicarbonate and then again with water. he chloroform phase was dried with anhydrous sodium sulfate, filtered, and the chloroform removed using a rotary evaporator to give 8 g of an oil. The oil was crystallized from a small amount of ethanol, with a melting point of 77–78° C., and a yield of 3 g (30%). IR spectrum showed the presence of $SO_2$ at 1160, 1310 $cm^{-1}$.

EXAMPLE 36

Preparation of 5-chloro-2(benzylthio)pyridine-N-oxide (Compound 151)

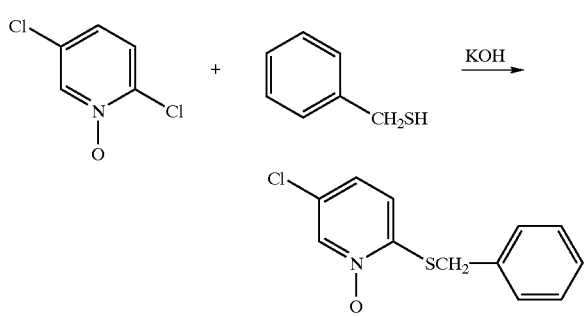

A solution consisting of 1.1 g (0.016 mole) of 85% KOH pellets, 50 ml of ethanol, and 0.5 ml of water was prepared. To this solution was added slowly, with stirring at room temperature, a mixture of 3.3 g (0.02 mole) of 2,5-dichloropyridine-N-oxide and 2.5 g (0.02 mole) of benzylmercaptan dissolved in 25 ml of ethanol. The reaction mixture was heated to about 60° C. for 2 hours and then evaporated to dryness. The residue was taken up in water and chloroform, the phases separated and the chloroform phase was dried over $Na_2SO_4$. The $Na_2SO_4$ was filtered off and the chloroform evaporated to leave a solid. The solid was recrystallized from ethanol to give 3.0 g of material, having a melting point of 130–133° C. Recovery was 2.2 g. The structure was confirmed by its IR spectrum.

EXAMPLE 37

Preparation of 2-(N-methyl-3-piperidylmethylthio)pyridine N-oxide (Compound 156)

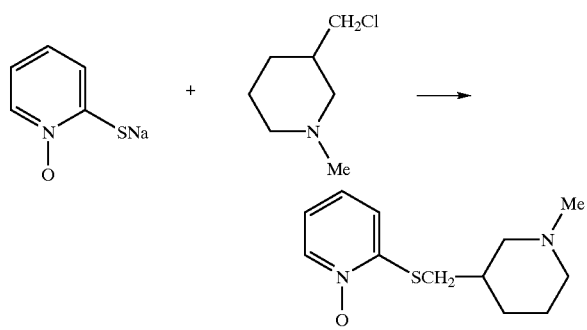

To 24.5 g (0.0675 mole) of sodium omidine (40% aqueous solution) dissolved in 50 ml of ethanol were added 10 g (0.0675 mole) of 3-chloromethyl-1-methylpiperidine. The mixture was stirred and warmed in a water bath at 58° C. for two hours and then allowed to stir overnight at room temperature. She mixture was then filtered to remove NaCl and the filtrate was evaporated on a rotovap. The remaining oil solid was treated with 50 ml of acetone and filtered to remove residual NaCl. Evaporation of the acetone left 15 g of oil. This was treated with dilute aqueous sodium hydroxide and chloroform. The phases were separated, the chloroform layer dried, and the chloroform then removed to leave 6 g of an amber liquid. An infrared spectrum was consistent with the structure of the product.

EXAMPLE 38

Preparation of 2-(2,5-dimethylphenylmethylthio) pyridine hydrochloride

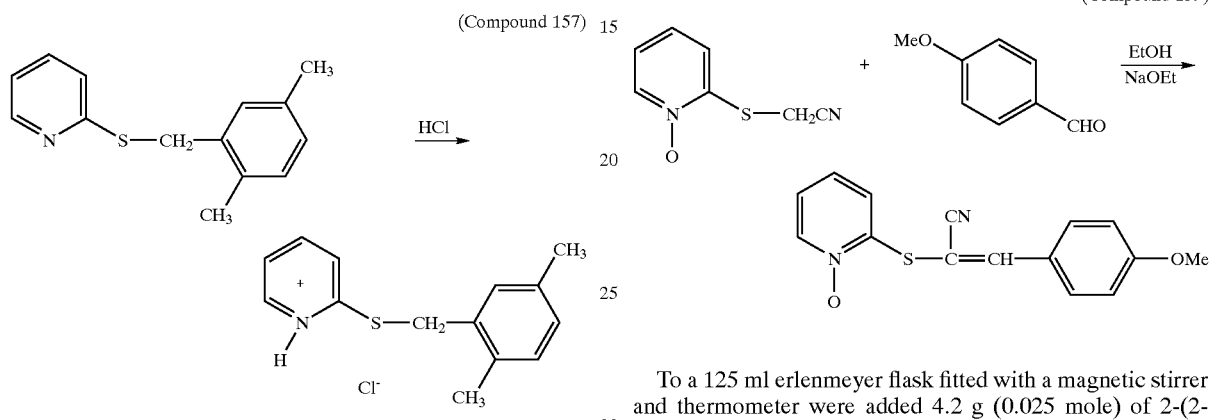

(Compound 157)

To 25 ml of water were added 10 ml of concentrated hydrochloric acid and then 4.6 g (0.02 mole) of 2-(2,5-dimethylphenylmethylthio)pyridine. The mixture was swirled and the water was then evaporated to leave a solid. The solid was taken up in ethanol and ether was then added to precipitate a yellow-colored solid. The solid was filtered off and then treated with boiling acetone and filtered while hot. Obtained 4 g of pale-yellow solid having a melting point of 83–85° C. An infrared spectrum indicated a pyridine hydrochloride by the broad peak at 2500 cm$^{-1}$, and peaks at 740 cm$^{-1}$ and 815 cm$^{-1}$ consistent with a pyridine ring.

EXAMPLE 39

Preparation of 2-(1-(cyano)-2-(phenylethenethio) pyridine-N-oxide

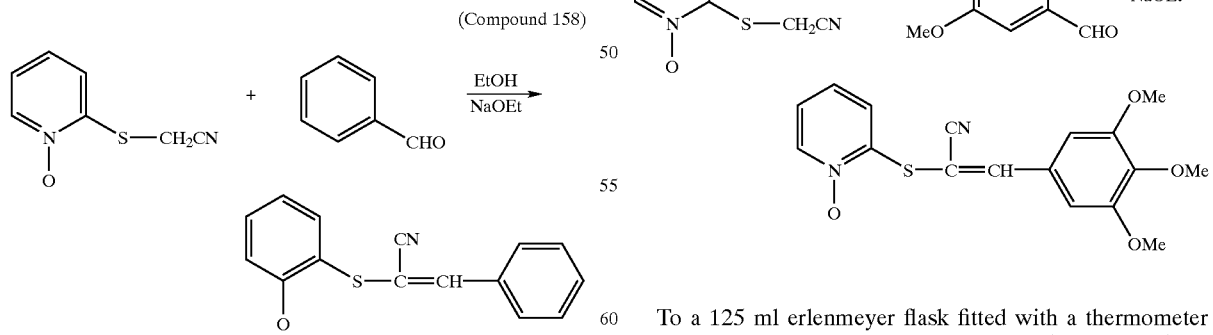

(Compound 158)

Ethanol (60 ml) and 0.5 g of sodium metal were added to a three-neck flask fitted with a magnetic stirrer, thermometer and condenser. The sodium was allowed to completely react with the ethanol to form sodium ethoxide. Then 4.2 g (0.025 mole) of 2-(1-cyanomethylthio)-pryridine-N-oxide was added followed by 2.7 g (0.025 mole) of benzaldehyde. The solution immediately turned orange, then red, and a precipitate formed. There was also a slight temperature increase from 27–36° C. After 15 minutes the batch was filtered to give a yellow solid having a melting point of 171–173° C. An NMR was consistent with the structure. Yield 2.9 g or 46%.

EXAMPLE 40

Preparation of 2-[1-cyano-2-(p-methoxyphenyl) ethenethio]pyridine-N-oxide (Compound 159)

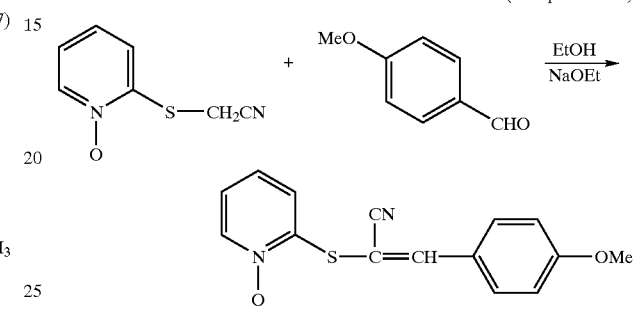

To a 125 ml erlenmeyer flask fitted with a magnetic stirrer and thermometer were added 4.2 g (0.025 mole) of 2-(2-cyanomethylthio)-pyridine-N-oxide, 3.4 g (0.025 mole) of 4-methoxybenzaldehyde, 60 ml of ethanol and 3 ml of sodium ethoxide solution in ethanol. The mixture was stirred at room temperature overnight and was then filtered to give 4.3 g (64.2%) of a white solid having a melting point of 169–172° C. The infrared spectrum was consistent with the structure, showing a CN absorption at 2200 cm$^{-1}$.

EXAMPLE 41

Preparation of 2-[1-cyano-2-(3,4,5-trimethoxyphenyl)ethenethio]pyridine-N-oxide (Compound 160)

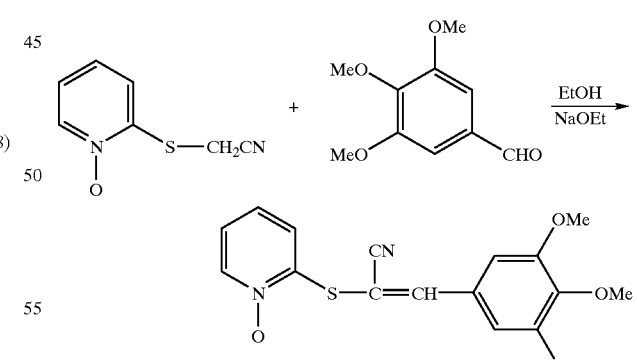

To a 125 ml erlenmeyer flask fitted with a thermometer and magnetic stirrer were added 4.2 g (0.025 mole) of 2-(1-cyanomethylthio)-pyridine-N-oxide, 4.9 g (0.025 mole) of 3,4,5-trimethoxybenzoldehyde, 60 ml of ethanol, and 3 ml of sodium ethoxide in ethanol. The batch developed a yellow, then orange color with the production of a very heavy precipitate within 10 minutes. A few ml of ethanol were added and the batch stirred for one hour before filtering. There was a temperature increase of only 3° C. (24–27°) during the reaction. A yellow solid was isolated having a melting point of 141–158° C. The crude material was recrystallized from ethanol to give a yellow solid having a melting point of 176–179° C., whose IR spectrum supported the proposed structure. There were 2.0 g isolated (23.2% yield).

EXAMPLE 42

Preparation of 2-[1-(2,5-dimethylphenyl)ethylsulfonyl]pyridine (Compound 161)

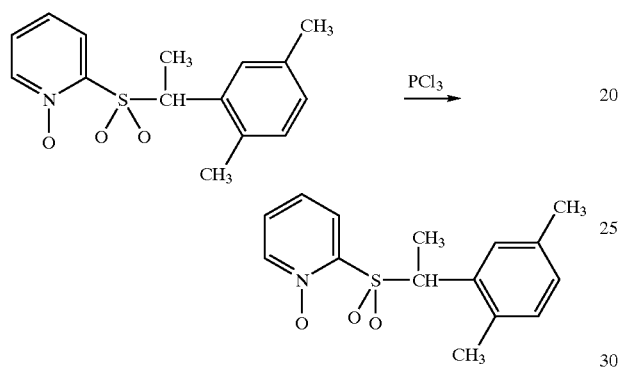

A mixture of 4.7 g (0.017 mole) of 2-[1-(2,5-Dimethylphenyl)-ethylsulfonyl]-pyridine-N-oxide, 60 ml of chloroform, and 7.5 g (0.055 mole) of PCl$_3$ were placed in a 100 ml round bottom flask equipped with a magnetic stirrer and reflux condenser. The mixture was refluxed for one hour, and then the solvent was removed under reduced pressure using a rotovap. To the residue was added 25 ml of ethanol, followed by a second evaporation. The residue crystallized to give a white solid, which was recrystallized from ethanol. Obtained were 3.0 g of product having a melting point of 95–96° C. The IR, NMR and mass spectra were consistent with the proposed structure.

EXAMPLE 43

Preparation of 2-[[1-(2,5-dimethylphenyl)ethyl]thio]-4-methylquinoline (Compound 162)

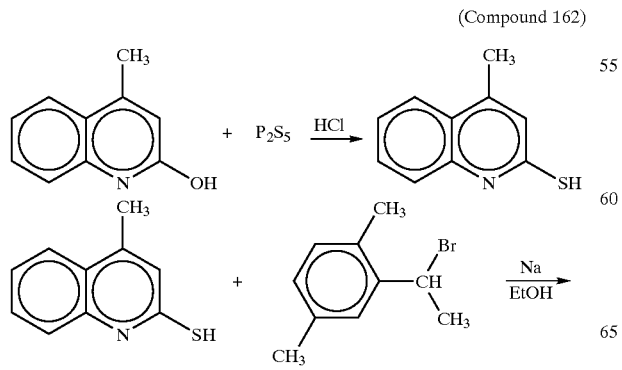

-continued

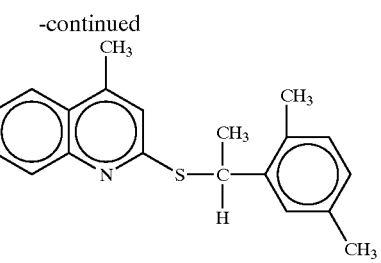

a) Preparation of 2-thio]-4-methylquinoline(starting material)

A mixture of 15.9 g of 2-hydroxy-4-methylquinoline and 24.4 g of P$_2$S$_5$ were heated together in an oil bath at 150° C. to give a homogeneous melt. The melt was cooled and then 100 ml of hydrochloric acid (90ml of concentrated HCl and 10 ml of 10% HCl) were added and the mixture was refluxed for two hours. The mixture was then filtered hot through a large buchner funnel using coarse filter paper. The yellow/orange solid was dried in a vacuum oven, melting point 250–253° C. An NMR spectrum indicated that it was the desired thiol.

b) Preparation of 2-[[1-(2,5dimethylphenyl)ethyl]thio]-4-methyl-Quinoline

Sodium (1.2 g) was dissolved in 50 ml of ethanol and then 9.5 g of 2-thiol-4-methylquinoline (prepared in accordance with step (a) above), and 11.6 g of 2,5-dimethylphenyl(2-bromoethyl)benzene were added while stirring. An additional 50 ml of ethanol was then added and the reaction mixture was heated on a steam bath for five minutes, and then it was filtered hot to remove some light brown precipitate. A reddish precipitate deposited in the cooled filtrate. This was filtered off and then taken up in carbon tetrachloride and water to remove sodium bromide. There was some material that was insoluble in both the organic and the water layer, and this was removed by filtration. The layers were separated and the carbon tetrachloride removed from the organic layer. The residue was crystallized from ethanol and then recrystallized from isopropanol, melting point of 84–85° C. An NMR spectrum was in agreement with the proposed structure. C,H,N calculated for C$_{20}$H$_{21}$NS: %C=78.14; %H=6.89; %N=4.56; Found: %C=78.13; %H=6.85; %N=4.46.

EXAMPLE 44

Preparation of 2-(2,5-dimethylphenyl)methylsulfinyl)pyridine (Compound 163)

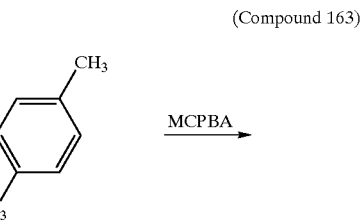

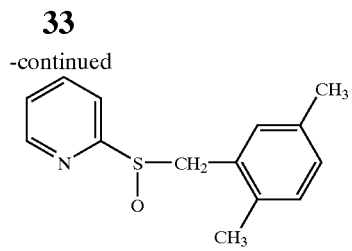

To a stirred and cooled solution (−10° C.) of 4.6 g (0.02mole) of 2-(2,5-dimethyl-phenyl)methylthio)pyridine in 50 ml of chloroform was added 4.1 g (0.02 mole) of 85% active metachloroperbenzoic acid in 50 ml of chloroform over a period of 30 minutes. The reaction mixture was stirred at 0° C. for 2 hours and then at ambient temperature overnight. The reaction mixture was washed with sodium bicarbonate, and then water. The chloroform phase was dried with magnesium sulfate, and the chloroform then removed using vacuum. A solid product (4.85 g or 98.5%) was obtained; melting point 77–79° C. It showed IR bands at 1050 and 1060 $cm^{-1}$ (S—O).

EXAMPLE 45

Activity against HIV

The cell type used to determine activity of the compounds of the invention herein, i.e., the test compounds, against HIV was human T-lymphoblast (CEM) cells obtained from the American Tissue Cell Culture Collection (Rockville, Md.). HIV-1 ($III_B$) was originally obtained from the culture of persistently HIV-1 infected H9 cells and was provided by R. C. Gallo and M. Popovic (National Cancer Institute, National Institutes of Health, Bethesda, Md.). HIV-2 (ROD) was originally obtained from L. M. Montagnier (Pasteur Institute, Paris, France).

To determine the antiviral activity of the test compounds, CEM cells were suspended at a cell density of approximately 300,000 cells per ml of culture medium and infected with approximately 100 $CCID_{50}$ (100 $CCID_{50}$ being the 50% cell culture infective dose) of HIV-1 (IIIB) or HIV-2 (ROD)). Then 100 μl of the infected cell suspensions was added to 200 μl micro titer plate wells containing 100 μl of appropriate serial (5-fold) dilutions of the test compounds. The inhibitory effect of the test compounds on HIV-1 or HIV-2 syncytium formation in CEM cells was examined microscopically on day four post infection. The 50% effective concentration ($EC_{50}$) was defined as the test compound concentration that inhibits syncytium formation in the HIV-1 or HIV-2 infected cell cultures by 50%.

In some cases, the compounds had considerable cytotoxicity to CEM cells which made determination of the $EC_{50}$ difficult. In these cases, the percent protection of the cells against virus-induced cytopathicity by the test compounds at the indicated compound concentration in the previous column is given.

The results are summarized in Table 1.

EXAMPLE 46

Activity against HCMV

Confluent HEL cells grown in 96-cell microtiter plates were inoculated with CMV at an input of 100 PFU (plaque forming units) per well. After a one to two hour incubation period, residual virus was removed and the infected cells were further incubated with MEM (Minimal Essential Medium) (supplemented with 2% inactivated Fetal Calf Serum (FCS), 2 μM L-glutamine, and 0.3% sodium bicarbonate) containing varying concentrations of the test compounds. Antiviral activity was expressed as $EC_{50}$ (50% effective concentration), or test compound concentration required to reduce virus-induced cytopathicity after seven days by 50% compared to the untreated control.

In some cases, the compounds had considerable cytotoxicity against HEL cells, which made determination of the $EC_{50}$'s difficult. In these cases, an estimate of the percent protection at the compound concentration indicated in the previous columns is given. The results are summarized in Table 1.

TABLE 1

| Compound No. | EC50 (μg/ml) HIV-1 | HIV-1 % Protection | EC50 (μg/ml) HIV-2 | HIV-2 % Protection | Antiviral IC50 (μg/ml) Davis strain | Antiviral % Inhibition Davis strain |
|---|---|---|---|---|---|---|
| 1 | 20.00 | | 41.0 | | >50 | 0.0 |
| 23 | ^20 | 37.5 | ^ 20 | 37.5 | >20 | 20.0 |
| 25 | 10.00 | | ^ 20 | 37.5 | 16.0 | |
| 40 | 3.10 | | 3.4 | | 1.5 | |
| 51 | >.8 | 0.0 | >.8 | 0.0 | 1.3 | |
| 60 | 40.00 | | 17.0 | | >50 | 0.0 |
| 61 | >4 | 0.0 | >4.0 | 6.0 | 14.0 | |
| 62 | 1.90 | | 5.0 | | >5 | 20.0 |
| 63 | 2.30 | | 2.5 | | 3.7 | |
| 64 | 1.50 | | 1.9 | | >5 | 10.0 |
| 65 | 2.80 | | 3.5 | | 5.0 | |
| 66 | 3.10 | | 2.5 | | 5.0 | |
| 67 | 2.30 | | 2.4 | | >50 | 20.0 |
| 69 | 2.90 | | 2.9 | | >5 | 20.0 |
| 73 | 2.80 | | >100.0 | 0.0 | >20 | 40.0 |
| 76 | 0.90 | | 2.4 | | >9.1 | |
| 77 | 0.70 | | >0.8 | 0.0 | 11.0 | |
| 81 | ^20 | 37.5 | >20.0 | 0.0 | 8.6 | |
| 106 | 0.90 | | >4.0 | 0.0 | 20.0 | |
| 107 | 0.65 | | >100 | | >20 | 0.0 |
| 123 | 60.00 | | >100 | 0.0 | >50 | 40.0 |
| 124 | >.8 | 0.0 | >0.80 | 0.0 | >5 | 10.0 |
| 125 | >4 | 0.0 | >4.0 | 0.0 | 31.5 | |
| 132 | 2.40 | | >20.00 | 0.0 | >50 | 0.0 |

TABLE 1-continued

| Compound No. | EC50 (µg/ml) HIV-1 | HIV-1 % Protection | EC50 (µg/ml) HIV-2 | HIV-2 % Protection | Antiviral IC50 (µg/ml) Davis strain | Antiviral % Inhibition Davis strain |
|---|---|---|---|---|---|---|
| 133 | 0.14 | | >20.00 | 0.0 | 25.0 | |
| 134 | >20 | 0.0 | >100.0 | 0.0 | >50 | |
| 136 | 1.50 | | >4.0 | 0.0 | 4.7 | |
| 137 | >20 | 0.0 | >20.00 | 0.0 | 28.0 | |
| 138 | >100 | 0.0 | >100.0 | 0.0 | >50 | 20.0 |
| 139 | >20 | 0.0 | >20.00 | 0.0 | 43.0 | |
| 142 | >4 | 0.0 | >4 | 0.0 | 3.4 | |
| 146 | 2.30 | | ^ 20 | 37.5 | 40.0 | |
| 148 | >20 | | >20 | | 0.4 | |
| 149 | 9.00 | | 16.0 | | 20.0 | |
| 150 | 3.25 | | 20.0 | | >50 | 20.0 |
| 151 | >20 | 0.0 | >20.00 | 0.0 | >20 | 20.0 |
| 156 | 16.00 | | >100 | 0.0 | >50 | 0.0 |
| 157 | 6.00 | | ^ 20 | 37.5 | >50 | 0.0 |
| 158 | >4 | 0.0 | >4 | 0.0 | 3.6 | |
| 159 | >20 | 0.0 | >20 | 25.0 | 10.0 | |
| 160 | >20 | 0.0 | >20 | 0.0 | 7.0 | |
| 161 | 9.50 | | >100 | 0.0 | 38.0 | |
| 162 | >.8 | 0.0 | >.16 | 0.0 | 1.6 | |
| 163 | 3.25 | | >100 | 0.0 | >50 | 0.0 |

^ Means greater or equal to

What is claimed is:

1. A compound selected from the group consisting of 2-[[1-(5-amino-2-methylphenyl)ethyl]sulfonyl]pyridine-N-oxide, 1,4xylyl-bis-2-sulfonyl pyridine-N-oxide, 1,4[1,2,4,5-tetramethylbenzyl]-bis-(2'-sulfonylpyridine-N-oxide), 2-(4'-tert-pentylphenylmethylsulfonyl)pyridine-N-oxide, 2[1-(9-anthryl)methylsulfonyl]pyridine-N-oxide, ethyl-N-[4-(pyridyl-N-oxide-2-sulfonylmethyl)phenylcarbonyl]carbamate, 2-[(3-methoxy-4-benzyloxy)phenylmethylsulfonyl]pyridine-N-oxide, 2-[[(2-nitro-5-methylphenyl)methyl]sulfonyl]pyridine-N-oxide, 2-[[[2,5-bis(1-methylethyl)-4-bromophenyl]methyl]sulfonyl]pyridine-N-oxide, 2-[[(3-nitro-4-chlorophenyl)methyl]sulfonyl]pyridine-N-oxide, 2-[[(3,5-dinitrophenyl)methyl]sulfonyl]pyridine-N-oxide, 2-[[(3-methyl-4-nitrophenyl)methyl]sulfonyl]pyridine-N-oxide, 2-[[(3-nitro-4-methylphenyl)methyl]sulfonyl]pyridine-N-oxide, 2-[[(2-chloro-4-nitrophenyl)methyl]sulfonyl]pyridine-N-oxide, 2-[(2,5-dimethylphenyl)chloromethylsulfonyl]-6-methylpyridine-N-oxide, 2-[1-(2,5-dimethylphenyl)ethylsulfonyl]-6-chloropyridine-N-oxide, 2-(2,5-dimethylphenylmethylsulfonyl)-6-chloropyridine-N-oxide, 2-[1-(2,5-dimethylphenyl)ethylsulfonyl]-4,6 dimethylpyridine-N-oxide, 2[(2,5-dimethylphenyl)chloromethylsulfonyl]pyridine, 8-ethyl4-methyl-2-[(1-phenylethyl)sulfonyl]quinoline, 2-[[1-(2,5-dimethylphenyl)-2-methoxyethyl]sulfonyl]pyridine, 3-chloro-2-[[1-(2,5-dimethylphenyl)ethyl]sulfonyl]pyridine-N-oxide, 3-chloro-2-[[chloro-(2,5-dimethylphenyl)methyl]sulfonyl]pyridine-N-oxide, 3-chloro-2-[(phenylmethyl)thio]pyridine-N-oxide, 3-chloro-2-[[(2,5-dimethylphenyl) methyl]thio]pyridine-N-oxide, 4-(1,1-dimethylethyl)-2-[(4-methoxyphenyl)methylthio]pyridine-N-oxide, 3-chloro-2-[(phenylmethyl)sulfinyl]pyridine-N-oxide, 2-[[(2,6-dichlorophenyl)methyl]thio]-3-methyl-pyridine-N-oxide, 2-[[(2,6-dichlorophenyl)methyl]sulfinyl]-3-methyl-pyridine-N-oxide, 2-[[(2,6-dichlorophenyl)methyl]sulfonyl]-3-methyl-pyridine-N-oxide, 2[[(2,5-dimethylphenyl)methyl]thio]-1-methylpyridinium chloride, 2-benzylthio-3-nitropyridine, 2-((2,5-dimethylphenyl)methylthio)pyridine, 6-chloro-(2-benzylthio)pyridine-N-oxide, 2-(2,5-dimethylbenzylsulfonyl)pyridine, 5-chloro-2(benzylthio)pyridine-N-oxide, 2-(N-methyl-3-piperidylmethylthio)pyridine-N-oxide, 2-(2,5-dimethylphenylmethylthio)pyridine hydrochloride, 2-(1-cyano-2-phenylethenethio)pyridine-N-oxide, 2-[1-cyano-2-(p-methoxyphenyl)ethenethio]pyridine-N-oxide, 2-[1-cyano-2-(3,4,5-trimethoxyphenyl)ethenethio]pyridine-N-oxide, 2-[1-(2,5-dimethylphenyl)ethylsulfonyl]pyridine, 2-[[1-(2,5-dimethylphenyl)ethyl]thio]-4-methylquinoline and 2-(2,5-dimethylphenyl)methylsulfinyl)pyridine and pharmaceutically acceptable salts thereof.

2. A composition comprising the compound of claim 1 and a pharmaceutically acceptable carrier.

\* \* \* \* \*